(12) United States Patent
Newcombe et al.

(10) Patent No.: US 7,465,728 B2
(45) Date of Patent: *Dec. 16, 2008

(54) DERIVATIVES OF 4-(IMIDAZOL-5-YL)-2-(4-SULFOANILINO) PYRIMIDINE WITH CDK INHIBITORY ACTIVITY

(75) Inventors: Nicholas John Newcombe, Macclesfield (GB); Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 390 days.

This patent is subject to a terminal disclaimer.

(21) Appl. No.: 10/507,081

(22) PCT Filed: Mar. 6, 2003

(86) PCT No.: PCT/GB03/00983

§ 371 (c)(1), (2), (4) Date: Sep. 9, 2004

(87) PCT Pub. No.: WO03/076436

PCT Pub. Date: Sep. 18, 2003

(65) Prior Publication Data

US 2005/0131000 A1     Jun. 16, 2005

(30) Foreign Application Priority Data

Mar. 9, 2002     (GB)     ............ 0205693.5

(51) Int. Cl.
C07D 403/04     (2006.01)
A61K 31/506     (2006.01)

(52) U.S. Cl. ............... 514/235.8; 514/255.05; 514/275; 544/122; 544/331

(58) Field of Classification Search .............. 514/235.8, 514/255.05, 275; 544/122, 331
See application file for complete search history.

(56) References Cited

U.S. PATENT DOCUMENTS

| | | | |
|---|---|---|---|
| 4,983,608 A | 1/1991 | Effland et al. | |
| 5,516,775 A | 5/1996 | Zimmermann et al. | |
| 5,521,184 A | 5/1996 | Zimmermann | |
| 5,610,303 A | 3/1997 | Kimura et al. | |
| 5,739,143 A | 4/1998 | Adams et al. | |
| 5,859,041 A | 1/1999 | Liverton et al. | |
| 6,835,726 B2 | 12/2004 | Cushing et al. | |
| 6,908,920 B2 | 6/2005 | Thomas et al. | |
| 6,969,714 B2 * | 11/2005 | Breault et al. ............. | 514/235.8 |
| 2003/0144303 A1 | 7/2003 | Hawley et al. | |
| 2003/0191307 A1 | 10/2003 | Blumenkopf et al. | |
| 2004/0102630 A1 | 5/2004 | Brumby et al. | |
| 2004/0224966 A1 | 11/2004 | Brumby et al. | |
| 2005/0176743 A1 | 8/2005 | Luecking et al. | |
| 2006/0079543 A1 | 4/2006 | Sum et al. | |
| 2006/0111378 A1 | 5/2006 | Cleve et al. | |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 945 443 A1 | 9/1999 |
| EP | 1056742 | 7/2003 |
| HU | 220630 | 3/2002 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/33798 | 8/1998 |
| WO | 98/41512 | 9/1998 |
| WO | 98/54093 | 12/1998 |

(Continued)

OTHER PUBLICATIONS

Traxler, Protein tyrosine kinase inhibitors in cancer treatment, Expert Opinion on Therapeutic Patents, 7(6), pp. 571-588, 1997.*

(Continued)

*Primary Examiner*—Deepak Rao
(74) *Attorney, Agent, or Firm*—Morgan, Lewis & Bockius LLP

(57) ABSTRACT

Compounds of the formula (I): wherein $R^1$, $R^2$, $R^3$, $R^4$, $R^5$ and p are as defined within and a pharmaceutically acceptable salts and in vivo hydrolysable esters are described. Also described are processes for their preparation and their use as medicaments, particularly medicaments for producing a cell cycle inhibitory (anti-cell-proliferation) effect in a warm-blooded animal, such as man.

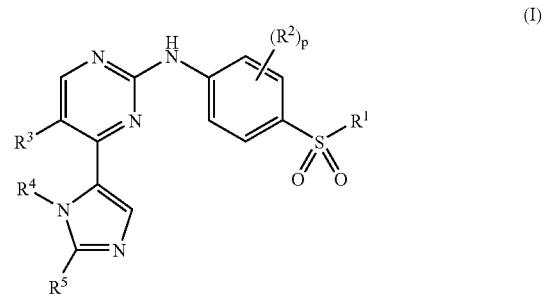

(I)

19 Claims, No Drawings

FOREIGN PATENT DOCUMENTS

| | | |
|---|---|---|
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 6/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 02/04429 A | 1/2002 |
| WO | 02/20512 A | 3/2002 |
| WO | WO 02/46170 | 6/2002 |
| WO | WO 02/46171 | 6/2002 |
| WO | 02/066481 A1 | 8/2002 |
| WO | WO 02/065979 | 8/2002 |
| WO | WO 02/066480 | 8/2002 |
| WO | WO 02/092573 | 11/2002 |
| WO | 02/096887 A1 | 12/2002 |
| WO | WO 02/096888 | 12/2002 |
| WO | 03/007955 A2 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | 03/076433 A1 | 9/2003 |
| WO | 03/076434 A1 | 9/2003 |
| WO | 03/076435 A1 | 9/2003 |
| WO | WO 2004/005283 | 1/2004 |
| WO | WO 2004/043467 | 5/2004 |
| WO | WO 2004/043953 | 5/2004 |
| WO | WO 2004/087698 | 10/2004 |
| WO | WO 2004/087699 | 10/2004 |
| WO | WO 2004/101549 | 11/2004 |
| WO | WO 2004/101564 | 11/2004 |
| WO | WO 2005/012298 | 2/2005 |
| WO | WO 2005/037800 | 4/2005 |
| WO | WO 2005/075461 | 8/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | WO 2007/036732 | 4/2007 |
| WO | WO 2007/040440 | 4/2007 |
| WO | WO 2007/138268 | 12/2007 |
| WO | WO 2007/138277 | 12/2007 |
| WO | WO 2007/148070 | 12/2007 |

OTHER PUBLICATIONS

Lu Valle et al., Cell Cycle Control in Growth Plate Chondrocytes, Frontiers in Biosciences 5, d493-503, May 2000.*

Boschelli et al., Synthesis and Tyrosine Kinase Inhibitory Activity of a Series of 2-Amino-8-$H$-pyrido[2,3-$d$]pyrimidines: Identification of Potent, Selective Platelet-Derived Growth Factor Receptor Tyrosine Kinase Inhibitors, J. Med. Chem., vol. 41, 1998, pp. 4365-4377.

Deady et al., "Reactions of some Quinazoline Compounds with Ethoxymethylenemalonic Acid Derivatives", J. Heterocyclic Chem., vol. 26, 1989, pp. 161-168.

El-Kerdawy et al.; "2,4-Bis (Substituted)-5-Nitropyrimidines of Expected Diuretic Action"; Egypt J. Chem. vol. 29, No. 2, 1986, pp. 247-251.

Fiziol Akt Veshchestva, 1975, vol. 7, pp. 68-72.

Ghosh et al.; "2,4-Bis(arylamino)-5-methylpyrimidines as Antimicrobial Agents"; J. Med. Chem., 1967, vol. 10, No. 5, pp. 974-975.

Ghosh, "2,4-Bis(Arylamino)-6-Methyl Pyrimidines as Antimicrobial Agents", J. Indian Chem. Soc., vol. 58, No. 5, 1981, pp. 512-513.

Schmidt et al.; "A Convenient Synthesis of 2-substituted 4-Amino-5-pyrimidinecarbonitriles"; J. Heterocycle Chem., 1997, vol. 24, No. 5, pp. 1305-1307.

Zimmermann et al., Phenylamino-Pyrimidine (PAP) Derivatives: A New Class of Potent and Selective Inhibitors of Protein Kinase C (PKC), Arch. Pharm. Pharm. Med. Chem., vol. 329, 1996, pp. 371-376.

Blain et al. "Differential Interaction of the Cyclin-dependent Kinase (Cdk) Inhibitor p27Kip1 with Cyclin A-Cdk2 and Cyclin D2-Cdk4" J. Biol. Chem. 272(41):25863-25872 (1997).

Simone, Oncology: Introduction, Cecil Textbook of Medicine, 20th Edition, vol. 1, pp. 1004-1010 (1996).

Volin et al. "Cell cycle implications in the pathogenesis of rheumatoid arthritis" Frontiers in Bioscience 5: D594-601(2000).

Fiziol Akt Veshchestva 7:68-72 (1975) (Translation enclosed).

* cited by examiner

DERIVATIVES OF 4-(IMIDAZOL-5-YL)-2-(4-SULFOANILINO) PYRIMIDINE WITH CDK INHIBITORY ACTIVITY

This application is a 371 of PCT/GB03/00983 filed Mar. 6, 2003.

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of the formula (IA), (IB), (IC), (ID), (IE) and (IF) of the following generic structure formula (I):

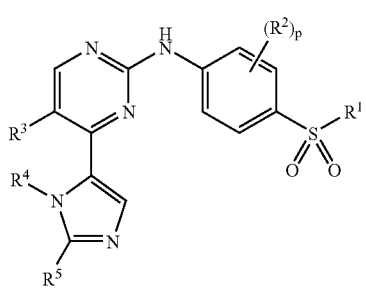

(I)

wherein $R^1$, $R^2$, $R^3$, $R^4$, $R^5$ and p are as defined below;

or a pharmaceutically acceptable salt or an in vivo hydrolysable ester thereof.

Specifically, according to the present invention there is provided a compound of formula (IA):

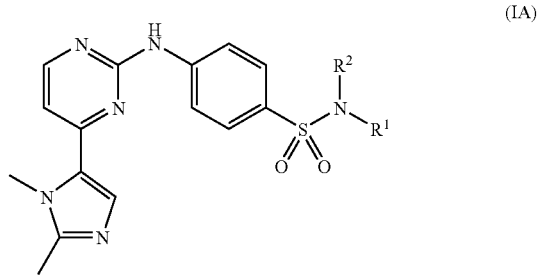

(IA)

wherein:

$R^1$ is 2-(pyrazolyl-1-yl)ethyl, 3-(isoxazol-3-yloxy)propyl, 2-(isothiazol-3-yloxy)ethyl, 2-(thiadiazol-3-yloxy)ethyl, 1,3-dihydroxyprop-2-yl, 1-methyl-1-hydroxymethylethyl, 1,1-dimethylpropyl, 1-methylcyclopropyl, t-butyl, 2-morpholino-1,1-dimethylethyl, 2-pyrrolidin-1-yl-1,1-dimethylethyl, 2-methylthio-1,1-dimethylethyl, 1,3-dimethoxyprop-2-yl, 1-methoxyprop-2-yl, 1-hydroxyprop-2-yl, 1-ethoxyprop-2-yl, 1-propoxyprop-2-yl, ethoxyethyl or 2-methoxy-1,1-dimethylethyl; and $R^2$ is hydrogen;

or $R^1$ and $R^2$ together form 2,2-dimethylaziridin-1-yl;

or a pharmaceutically acceptable salt or an in vivo hydrolysable ester thereof.

According to a further aspect of the present invention there is provided a compound of formula (IB):

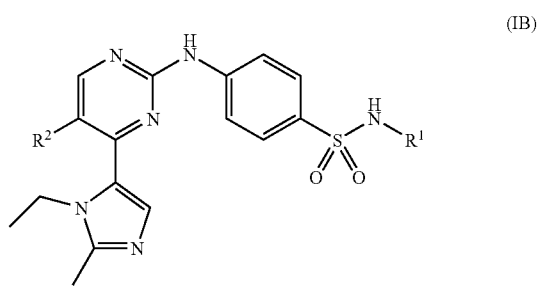

(IB)

wherein:

$R^1$ is pyrid-2-ylmethyl, 2-(2-methyl-1,2,4-triazol-5-yl) ethyl, 2-pyrid-2-ylethyl, 2-pyridazin-3-ylethyl, 2-(3,5-dimethyltriazol-4-yl)ethyl, 2-pyrid-3-ylethyl, 2-methoxyethyl, 3-(5-methylpyrazol4-yl)propyl, 2-trifluoromethylpyrid-5-ylmethyl, 2-pyridazin-4-ylethyl, 1,1-dimethylprop-2-ynyl, 2-ethoxyethyl, 2-phenoxyethyl, 2-(4-methoxyphenoxy) ethyl, 2-(2-methoxyphenoxy)ethyl, 2-(vinyloxy)ethyl, 2-(isopropoxy)ethyl and 2-(propoxy)ethyl; and $R^2$ is hydrogen or cyano;

or a pharmaceutically acceptable salt or an in vivo hydrolysable ester thereof;

provided that when $R^1$ is 2-methoxyethyl, $R^2$ is cyano.

According to a further aspect of the present invention there is provided a compound of formula (IC):

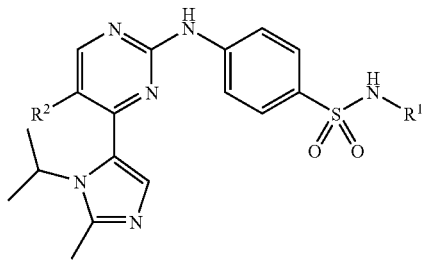

(IC)

wherein:

R[1] is hydrogen, heterocyclyl, $C_{1-6}$alkyl or $C_{1-6}$alkoxy$C_{1-6}$alkyl; wherein R[1] may be optionally substituted on carbon by one or more hydroxy, carboxy, $C_{1-6}$alkoxy, $C_{1-6}$alkoxycarbonyl, N,N-($C_{1-6}$alkyl)$_2$amino, heterocyclyl, $C_{3-6}$cycloalkyl and $C_{1-6}$alkoxy$C_{1-6}$alkoxy; and wherein if a heterocyclyl contains an —NH— moiety, that nitrogen may be optionally substituted by $C_{1-6}$alkyl or benzyl;

R[2] is hydrogen, halo or cyano;

or a pharmaceutically acceptable salt or an in vivo hydrolysable ester thereof;

provided that when R[1] is 2-methoxyethyl, cyclopropylmethyl or pyrid-2-ylmethyl, R[2] is not hydrogen.

According to a further aspect of the present invention there is provided a compound of formula (ID):

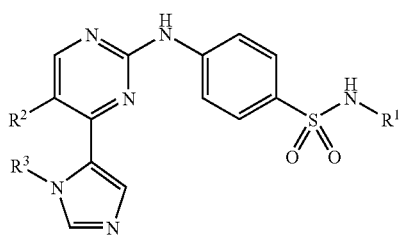

(ID)

wherein:

R[1] is hydrogen, $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein R[1] may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

R[2] is hydrogen, halo or cyano;

R[3] is $C_{2-6}$alkyl;

or a pharmaceutically acceptable salt or an in vivo hydrolysable ester thereof.

According to a further aspect of the present invention there is provided a compound of formula (IE):

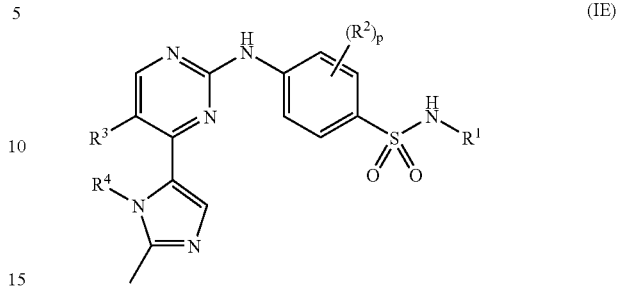

(IE)

wherein:

R[1] is hydrogen, $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein R[1] may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one, or more methyl, ethyl, acetyl, 2,2,2-trifluoroethyl or methoxyethyl;

R[2] is halo, cyano, $C_{1-3}$alkyl or $C_{1-3}$alkoxy;

p is 1-2; wherein the values of R[2] may be the same or different;

R[3] is hydrogen, halo or cyano;

R[4] is $C_{1-4}$alkyl;

or a pharmaceutically acceptable salt or an in vivo hydrolysable ester thereof; provided that said compound is not 4-(1,2-dimethylimidazol-5-yl)-2-[2-methoxy-4-(N-methylsulphamoyl)-5-methylanilino]-pyrimidine.

According to a further aspect of the present invention there is provided a compound of formula (IF):

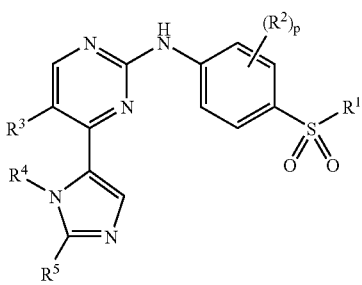

(IF)

wherein:

R[1] is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein R[1] may be optionally substituted on carbon by one or more methyl, ethyl, methoxy, ethoxy, propoxy, trifluoromethyl, trifluoromethoxy, dimethylamino, 2,2,2-trifluoroethoxy, phenyl or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^2$ is halo, cyano, $C_{1-3}$alkyl or $C_{1-3}$alkoxy;

p is 0-2; wherein the values of $R^2$ may be the same or different;

$R^3$ is hydrogen, halo or cyano;

$R^4$ is $C_{2-6}$alkyl;

$R^5$ is $C_{1-6}$alkyl or $C_{2-6}$alkenyl; wherein $R^5$ may be optionally substituted on carbon by one or more methoxy, ethoxy, propoxy, trifluoromethyl, trifluoromethoxy, 2,2,2-trifluoroethoxy or cyclopropylmethoxy;

or a pharmaceutically acceptable salt or an in vivo hydrolysable ester thereof.

According to a further aspect of the present invention there is provided a compound of formula (IG):

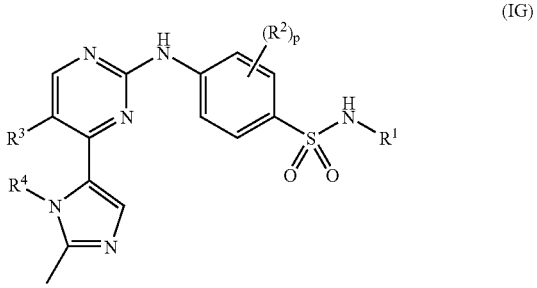

(IG)

wherein:

$R^1$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein $R^1$ may be optionally substituted on carbon by one or more methyl, ethyl, methoxy, ethoxy, propoxy, trifluoromethyl, trifluoromethoxy, dimethylamino, 2,2,2-trifluoroethoxy, phenyl or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^2$ is halo, cyano, $C_{1-3}$alkyl or $C_{1-3}$alkoxy;

p is 0-2; wherein the values of $R^2$ may be the same or different;

$R^3$ is hydrogen, halo or cyano;

$R^4$ is n-propyl or $C_{4-6}$alkyl;

or a pharmaceutically acceptable salt or an in vivo hydrolysable ester thereof.

In another aspect of the invention there is provided a compound of formula (IA) (as depicted above) wherein:

$R^1$ is 2-(pyrazolyl-1-yl)ethyl, 3-(isoxazol-3-yloxy)propyl, 2-(thiazol-3-yloxy)ethyl, 2-(thiadiazol-3-yloxy)ethyl, 1,3-dihydroxyprop-2-yl, 1-methyl-1-hydroxymethylethyl, 1,2-dimethylpropyl, 1-methylcyclopropyl, 2,2-dimethylaziridin-1-yl, t-butyl, 2-morpholino-1,1-dimethylethyl, 2-pyrrolidin-1-yl-1,1-dimethylethyl, 2-methylthio-1,1-dimethylethyl, 1,3-dimethoxyprop-2-yl, 1-methoxyprop-2-yl, 1-hydroxyprop-2-yl, 1-ethoxyprop-2-yl, 1-propoxyprop-2-yl, ethoxyethyl or 2-methoxy-1,1-dimethylethyl; and $R^2$ is hydrogen;

or a pharmaceutically acceptable salt or an in vivo hydrolysable ester thereof.

In another aspect of the present invention there is provided a compound of formula (IB) (as depicted above) wherein:

$R^1$ is pyrid-2-ylmethyl, 2-(2-methyl-1,2,4-triazol-5-yl) ethyl, 2-pyrid-2-ylethyl, 2-pyridazin-3-ylethyl, 2-(3,5-dimethyltriazol-4-yl)ethyl, 2-pyrid-3-ylethyl, 2-methoxyethyl, 3-(5-methylpyrazol-4-yl)propyl, 2-trifluoromethylpyrid-5-ylmethyl, 2-pyridazin-4-ylethyl, 1,1-dimethylpropyn-2-yl or 2-ethoxyethyl; and $R^2$ is hydrogen or cyano;

or a pharmaceutically acceptable salt or an in vivo hydrolysable ester thereof;

provided that when $R^1$ is 2-methoxyethyl, $R^2$ is cyano.

In another aspect of the present invention there is provided a compound of formula (IC) (as depicted above) wherein:

$R^1$ is hydrogen, $C_{1-6}$alkyl or $C_{1-6}$alkoxy$C_{1-6}$alkyl; and $R^2$ is hydrogen, halo or cyano;

or a pharmaceutically acceptable salt or an in vivo hydrolysable ester thereof;

provided that when $R^1$ is 2-methoxyethyl, $R^2$ is not hydrogen.

In another aspect of the present invention there is provided a compound of formula (IF) (as depicted above) wherein:

$R^1$ is $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$ alkyl; wherein $R^1$ may be optionally substituted on carbon by one or more methyl, ethyl, methoxy, ethoxy, propoxy, trifluoromethyl, trifluoromethoxy, dimethylamino, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

$R^2$ is halo, cyano, $C_{1-3}$alkyl or $C_{1-3}$alkoxy;

p is 0-2; wherein the values of $R^2$ may be the same or different;

$R^3$ is hydrogen, halo or cyano;

$R^4$ is $C_{2-6}$alkyl;

$R^5$ is $C_{1-6}$-alkyl or $C_{2-6}$alkenyl; wherein $R^5$ may be optionally substituted on carbon by one or more methoxy, ethoxy, propoxy, trifluoromethyl, trifluoromethoxy, 2,2,2-trifluoroethoxy or cyclopropylmethoxy;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl", "$C_{2-6}$alkyl", "$C_{1-4}$alkyl" and "$C_{1-3}$alkyl" include ethyl, propyl and isopropyl. Examples of "$C_{4-6}$alkyl" include t-butyl, isobutyl and sec-butyl. However, references to individual alkyl groups such as 'propyl' are specific for the straight chained version only and references to individual branched chain alkyl groups such as 'isopropyl' are specific for the branched chain version only. A similar convention applies to other radicals, for example "$C_{3-6}$cycloalkyl$C_{1-3}$alkyl" includes cyclopropylmethyl, 1-cyclobutylethyl and 2-cyclopentylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, monocyclic ring containing 4-6 atoms of which at least one atom is chosen from nitrogen, sulphur or oxygen, which may, unless otherwise specified, be carbon or nitrogen linked, and a ring sulphur atom may be optionally oxidised to form the S-oxide(s). Examples and suitable values of the term "heterocyclyl" are morpholino, piperidyl, pyridyl, pyranyl, pyrrolyl, isothiazolyl, thienyl, thiadiazolyl, piperazinyl, thiazolidinyl, thiomorpholino, pyrrolinyl, tetrahydropyranyl, to tetrahydrofuryl, imidazolyl, pyrimidyl, pyrazinyl, pyridazinyl and isoxazolyl. Suitably a "heterocyclyl" is tetrahydrofuryl. In another aspect of the invention, suitably "heterocyclyl" is pyrrolidinyl, morpholino, piperidinyl or tetrahydrofuryl.

Examples of "$C_{1-6}$alkoxy" and "$C_{1-3}$alkoxy" include methoxy, ethoxy and propoxy. Examples of "$C_{1-6}$alkoxycarbonyl" include methoxycarbonyl, ethoxycarbonyl and t-butoxycarbonyl. Examples of "N,N-($C_{1-6}$alkoxy)$_2$amino" include dimethylamino, diethylamino and methylethylamino. Examples of "$C_{2-6}$alkenyl" and "$C_{2-4}$alkenyl" are vinyl, allyl and 1-propenyl. Examples of "$C_{2-4}$alkynyl" are ethynyl, 1-propynyl and 2-propynyl. Examples of "$C_{3-6}$cycloalkyl" are cyclopropyl, cyclobutyl, cyclopentyl and cyclohexyl. Examples of "heterocyclyl$C_{1-3}$alkyl" include pyridylmethyl, 3-morpholinopropyl and 2-pyrimid-2-ylethyl. Examples of "$C_{1-6}$alkoxy$C_{1-6}$alkyl" are 2-methoxyethyl, ethoxymethyl, 2-ethoxypropyl and 2-ethoxyethyl. Examples of "$C_{1-6}$alkoxy$C_{1-6}$alkoxy" are 2-methoxyethoxy, ethoxymethoxy, 2-ethoxypropoxy and 2-ethoxyethoxy.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or, hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that-possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Suitable values of $R^1$, $R^2$, $R^3$, $R^4$, $R^5$ and p are as follows. Such values may be used where appropriate with any of the definitions, claims or embodiments defined hereinbefore or hereinafter.

For Compounds of Formula (IC).

$R^1$ is hydrogen or $C_{1-6}$alkoxy$C_{1-6}$alkyl.

$R^1$ is methyl, methoxyethyl or ethoxyethyl.

$R^1$ is hydrogen, methyl, ethyl, propyl, 2-methoxyethyl, 2-ethoxyethyl, 2-propoxyethyl, 2-isopropoxyethyl, 3-(t-butoxy)propyl, 3-ethoxypropyl and piperidinyl; wherein $R^1$ may be optionally substituted on carbon by one or more hydroxy, carboxy, methoxy, methoxycarbonyl, t-butoxycarbonyl, dimethylamino, diethylamino, cyclopropyl, 2-ethoxyethoxy, pyrrolidinyl, morpholino or piperidinyl; and wherein if said pyrrolidinyl or piperidinyl contains an —NH— moiety, that nitrogen may be optionally substituted by methyl, ethyl or benzyl.

$R^1$ is hydrogen, 2-methoxyethyl, methyl, 2-ethoxyethyl, 2-isopropoxyethyl, 2-propoxyethyl, 2-(cyclopropylmethoxy)ethyl, 3-(t-butoxy)propyl, 3-[2-(2-ethoxyethoxy)ethoxy]propyl, 3-(2-methoxyethoxy)propyl, carboxymethyl, t-butoxycarbonylmethyl, 2-hydroxyethyl, 2-(N-methylpyrrolidin-2-yl)ethyl, N-ethylpyrrolidin-2-ylmethyl, 2-pyrrolidin-1-ylethyl, 2-morpholinoethyl, 3-morpholinopropyl, N-benzylpiperidin4-yl, 2-piperdin-1-ylethyl, 2-dimethylaminoethyl, 2-diethylaminoethyl or methoxycarbonylmethyl.

$R^2$ is hydrogen or halo.

$R^2$ is hydrogen or bromo.

A compound of formula (IC) (as depicted above) wherein:
$R^1$ is hydrogen, methyl, ethyl, propyl, 2-methoxyethyl, 2-ethoxyethyl, 2-propoxyethyl, 2-isopropoxyethyl, 3-(t-butoxy)propyl, 3-ethoxypropyl and piperidinyl; wherein $R^1$ may be optionally substituted on carbon by one or more hydroxy, carboxy, methoxy, methoxycarbonyl, t-butoxycarbonyl, dimethylamino, diethylamino, cyclopropyl, 2-ethoxyethoxy, pyrrolidinyl, morpholino or piperidinyl; and wherein if said pyrrolidinyl or piperidinyl contains an —NH— moiety, that nitrogen may be optionally substituted by methyl, ethyl or benzyl; and $R^2$ is hydrogen or halo;

or a pharmaceutically acceptable salt or an in vivo hydrolysable ester thereof;

provided that when $R^1$ is 2-methoxyethyl or cyclopropylmethyl $R^2$ is not hydrogen.

A compound of formula (IC) (as depicted above) wherein:
$R^1$ is hydrogen, 2-methoxyethyl, methyl, 2-ethoxyethyl, 2-isopropoxyethyl, 2-propoxyethyl, 2-(cyclopropylmethoxy)ethyl, 3-(t-butoxy)propyl, 3-[2-(2-ethoxyethoxy)ethoxy]propyl, 3-(2-methoxyethoxy)propyl, carboxymethyl, t-butoxycarbonylmethyl, 2-hydroxyethyl, 2-(N-methylpyrrolidin-2-yl)ethyl, N-thylpyrrolidin-2-ylmethyl, 2-pyrrolidin-1-ylethyl, 2-morpholinoethyl, 3-morpholinopropyl, N-benzylpiperidin-4-yl, 2-piperdin-1-ylethyl, 2-dimethylaminoethyl, 2-diethylaminoethyl or methoxycarbonylmethyl; and
$R^2$ is hydrogen or bromo;

or a pharmaceutically acceptable salt or an in vivo hydrolysable ester thereof;

provided that when $R^1$ is 2-methoxyethyl $R^2$ is not hydrogen.

For Compounds of Formula (ID).
$R^1$ is $C_{1-4}$alkyl, $C_{3-6}$cycloalkyl or heterocyclyl$C_{1-3}$alkyl; wherein $R^1$ may be optionally substituted on carbon by one methoxy.
$R^1$ is cyclopropyl, 2-methoxyethyl or tetrahydrofur-2-ylmethyl.
$R^1$ is $C_{1-4}$alkyl, $C_{3-6}$cycloalkyl or heterocyclyl$C_{1-3}$alkyl; wherein $R^1$ may be optionally substituted on carbon by one or more methoxy or ethoxy.
$R^1$ is cyclopropyl, 2-methoxyethyl, 2-ethoxyethyl or tetrahydrofur-2-ylmethyl.
$R^2$ is hydrogen.
$R^3$ is ethyl or isopropyl.
$R^3$ is ethyl, propyl or isopropyl.
A compound of formula (ID) (as depicted above) wherein:
$R^1$ is $C_{1-4}$alkyl, $C_{3-6}$cycloalkyl or heterocyclyl$C_{1-3}$alkyl; wherein $R^1$ may be optionally substituted on carbon by one or more methoxy or ethoxy;
$R^2$ is hydrogen; and
$R^3$ is ethyl, propyl or isopropyl;

or a pharmaceutically acceptable salt or an in vivo hydrolysable ester thereof.

A compound of formula (ID) (as depicted above) wherein:
$R^1$ is cyclopropyl, 2-methoxyethyl, 2-ethoxyethyl or tetrahydrofur-2-ylmethyl;
$R^2$ is hydrogen; and
$R^3$ is ethyl, propyl or isopropyl;

or a pharmaceutically acceptable salt or an in vivo hydrolysable ester thereof.

For Compounds of Formula (IE).
$R^1$ is hydrogen or $C_{1-4}$alkyl; wherein $R^1$ may be optionally substituted on carbon by one methoxy.
$R^1$ is hydrogen or 2-methoxyethyl.
$R^2$ is halo.
$R^2$ is fluoro.
p is 1.
$R^3$ is hydrogen.
$R^4$ is methyl.
A compound of formula (IE) (as depicted above) wherein:
$R^1$ is hydrogen or $C_{1-4}$alkyl; wherein $R^1$ may be optionally substituted on carbon by one methoxy;
$R^2$ is halo;
p is 1;
$R^3$ is hydrogen; and
$R^4$ is methyl;

or a pharmaceutically acceptable salt or an in vivo hydrolysable ester thereof.

A compound of formula (IE) (as depicted above) wherein:
$R^1$ is hydrogen or 2-methoxyethyl;
$R^2$ is fluoro;
p is 1;
$R^3$ is hydrogen; and
$R^4$ is methyl;

or a pharmaceutically acceptable salt or an in vivo hydrolysable ester thereof.

For Compounds of Formula (IF).
$R^1$ is $C_{1-4}$alkyl; wherein $R^1$ may be optionally substituted on carbon by one or more methoxy, trifluoromethyl or dimethylamino.
$R^1$ is methyl, 3-dimethylaminopropyl, 3-methoxypropyl, 3,3,3-trifluoropropyl or butyl.
$R^1$ is $C_{1-4}$alkyl or heterocyclyl$C_{1-3}$alkyl; wherein $R^1$ may be optionally substituted on carbon by one or more methoxy, ethoxy, trifluoromethyl, dimethylamino or phenyl.
$R^1$ is methyl, 3-dimethylaminopropyl, 3-methoxypropyl, 3,3,3-trifluoropropyl, butyl, benzyl, tetrahydrofur-2-ylmethyl, 3-ethoxypropyl or 3-morpholinopropyl.
p is 0.
$R^3$ is hydrogen.
$R^3$ is hydrogen or halo.
$R^3$ is hydrogen or bromo.
$R^4$ is isopropyl.
$R^5$ is methyl.
A compound of formula (IF) (as depicted above) wherein:
$R^1$ is $C_{1-4}$alkyl or heterocyclyl$C_{1-3}$alkyl; wherein $R^1$ may be optionally substituted on carbon by one or more methoxy, ethoxy, trifluoromethyl, dimethylamino or phenyl;
p is 0;
$R^3$ is hydrogen or halo;
$R^4$ is isopropyl; and
$R^5$ is methyl;

or a pharmaceutically acceptable salt or an in vivo hydrolysable ester thereof.

A compound of formula (IF) (as depicted above) wherein:
$R^1$ is methyl, 3-dimethylaminopropyl, 3-methoxypropyl, 3,3,3-trifluoropropyl, butyl, benzyl, tetrahydrofur-2-ylmethyl, 3-ethoxypropyl or 3-morpholinopropyl.
p is 0;
$R^3$ is hydrogen or bromo;
$R^4$ is isopropyl; and
$R^5$ is methyl;

or a pharmaceutically acceptable salt or an in vivo hydrolysable ester thereof.

For Compounds of Formula (IG).
$R^1$ is $C_{1-4}$alkyl or $C_{3-6}$cycloalkyl; wherein $R^1$ may be optionally substituted on carbon by one or more methoxy or ethoxy.
$R^1$ is 2-methoxyethyl, 2ethoxyethyl or cyclopropyl.
p is 0.
$R^3$ is hydrogen.
$R^4$ is n-propyl or isobutyl.
A compound of formula (IG) (as depicted above) wherein:
$R^1$ is $C_{1-4}$alkyl or $C_{3-6}$cycloalkyl; wherein $R^1$ may be optionally substituted on carbon by one or more methoxy or ethoxy;
p is 0;
$R^3$ is hydrogen; and
$R^4$ is n-propyl or isobutyl;

or a pharmaceutically acceptable salt or an in vivo hydrolysable ester thereof.

$R^1$ is 2-methoxyethyl, 2-ethoxyethyl or cyclopropyl;
p is 0;
$R^3$ is hydrogen; and
$R^4$ is n-propyl or isobutyl;

or a pharmaceutically acceptable salt or an in vivo hydrolysable ester thereof.

In another aspect of the invention, particular compounds of the invention are any one of the Examples or a pharmaceutically acceptable salt or an in vivo hydrolysable ester thereof.

A particular aspect of the invention is that which relates to the compound of formula (I) or a pharmaceutically acceptable salt thereof.

For the avoidance of doubt, any aspect of the invention described herein that refers to a compound of formula (I) also relates to a compound of formula (IA), (IB), (IC), (ID), (IE), (IF) or (IG).

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, $R^5$ and p are, unless otherwise specified, as defined in formula (I), or wherein if any of $R^1$, $R^2$, $R^3$, $R^4$, $R^5$ and p are not defined in formula (I) $R^1$, $R^2$, $R^3$, $R^4$, and/or $R^5$ are hydrogen and/or p is 0) comprises of:

Process a) reaction of a pyrimidine of formula (II):

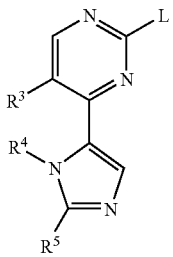

(II)

wherein L is a displaceable group; with an aniline of formula (III):

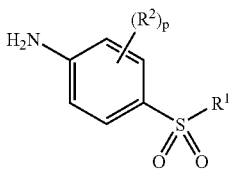

(III)

or

Process b) reacting a compound of formula (IV):

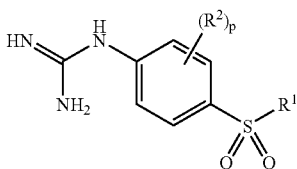

(IV)

with a compound of formula (V):

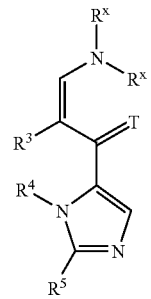

(V)

wherein T is O or S; $R^x$ may be the same or different and is $C_{1-6}$alkyl;

Process c) for compounds of formula (I) where $R^1$ is amino or a group $R^1$—$NH_2$—; reacting a pyrimidine of formula (VI):

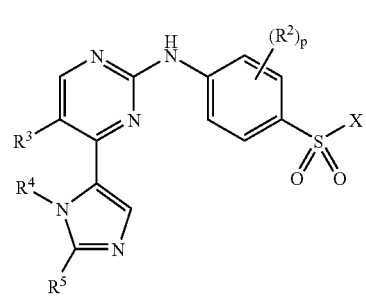

(VI)

wherein X is a displaceable group; with an amine of formula (VII):

$$R^a-NH_2 \qquad (VII)$$

wherein $R^a$ is hydrogen or $R^1$;

Process d) reacting a pyrimidine of formula (VIII)

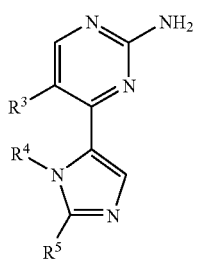

(VIII)

with a compound of formula (IX):

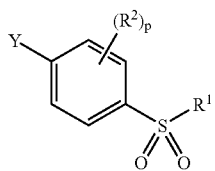

where Y is a displaceable group;

Process e) for compounds of formula (IF); oxidising a compound of formula (X):

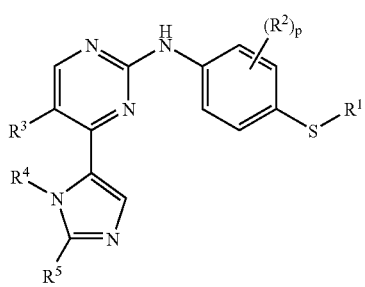

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for X are for example, a fluoro or chloro group. Preferably X is fluoro.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of formula (II) and anilines of formula (III) may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

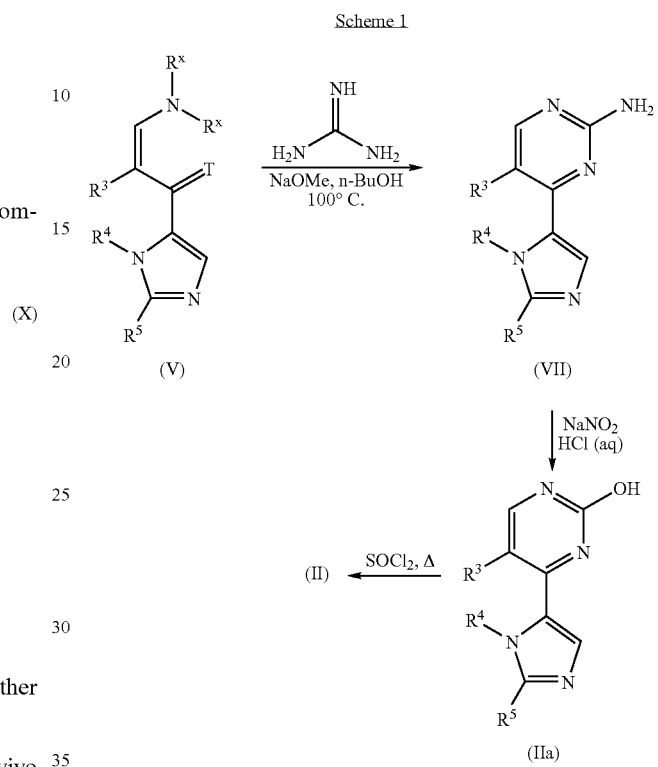

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

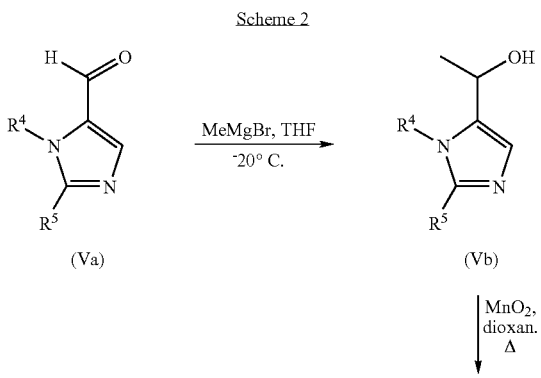

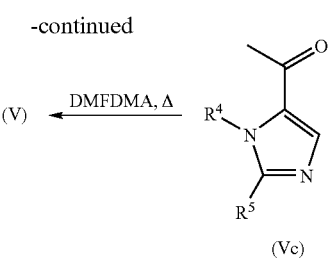

Compounds of formula (IV) and (Va) are commercially available compounds, or they are known in the literature, or they are prepared by standard processes known in the art.

Process c) Compounds of formula (VI) and amines of formula (VII) may be reacted together in the presence of an inert solvent such as N-methylpyrrolidinone or pyridine, in the presence of a base for example an inorganic base such as caesium carbonate or in the presence of an organic base such as excess (VII) and at a temperature in the range of 25 to 80° C.

Compounds of formula (VI) (wherein X is chloro) may be prepared according to Scheme 3:

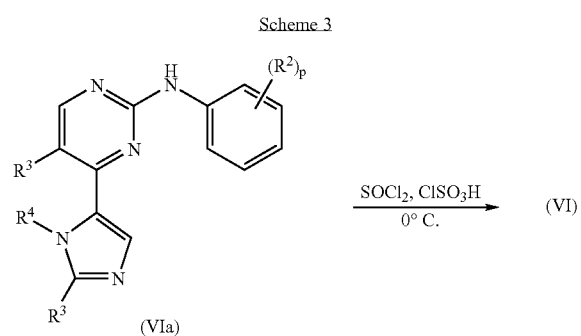

Compounds of formula (VIa) may be prepared according to Process a, Process b or Process d but wherein compounds (III), (IV) and (IX) are not substituted by $R^1SO_2$—.

Process d) Compounds of formula (VIII) and amines of formula (IX) may be reacted together under standard Buchwald conditions as described in Process a.

The synthesis of compounds of formula VIII) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

Process e) Compounds of formula (X) may be oxidised under standard sulphur oxidation conditions; for example using hydrogen peroxide and trifluoroacetic acid at a temperature, or oxone in methanol and acetone; or titanium isopropoxide and cumene hydroperoxide in butyl acetate; at a temperature in the range of 0° C. to reflux, preferably at or near room temperature.

Compounds of formula (X) may be prepared using a process described above for the preparation of a compound of formula (IF) but wherein the sulphone of formula (IF) is a sulphide.

In one aspect of the invention, there is provided a process for preparing a compound of formula (I) which is a process selected from Process a), Process b), Process c) or Process d).

In another aspect of the invention, there is provided a process for preparing a compound of formula (IF) which is Process e).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedures set out in WO 02/04429 (corresponding to U.S. Pat. No. 6,908,920).

Although the pharmacological properties of the compounds of the formula (I) vary with structural change, in general activity possessed by compounds of the formula (I) may be demonstrated at $IC_{50}$ concentrations or doses in the range 250 μM to 1 nM in the in vitro assay described in WO 02/04429.

Typical $IC_{50}$ values for compounds of the invention when tested in the SRB assay described in WO 02/04429 are in the range 1 mM to 1 nM.

According to a further aspect of the invention there is provided a pharmaceutical composition which comprises a pyrimidine derivative of the formula (I), or a pharmaceutically acceptable, salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those turnouts which are significantly dependent on CDKs for their growth and spread, including for example, certain tumours of the colon, breast, prostate, lung, vulva and skin. Particularly "cancer" is selected from leukaemia, breast cancer, lung cancer, colorectal cancer, stomach cancer, prostate cancer, bladder cancer, pancreatic cancer, ovarian cancer, liver cancer, kidney cancer, skin cancer and cancer of the vulva.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide, and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:

a) a compound of formula (I), or a pharmaceutically acceptable salt or in vivo hydrolysable ester thereof, in a first unit dosage form;

b) a pharmaceutical agent for treating malignant conditions that is known to cause hair loss; in a second unit dosage form; and c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

Some of the intermediates described herein are novel and are thus provided as a further aspect of the invention. For example, an additional aspect of the invention refers to a compound of formula (X). A particular compound of formula (X) is 4-(1-isopropyl-2-methylimidazol-5-yl)-2-[4-(methylthio)anilino]pyrimidine (Method 86).

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| DMFDMA | dimethylformamide dimethylacetal; |
| DMF | dimethylformamide; |
| EtOAc | ethyl acetate; |
| ether | diethyl ether; |
| MeOH | methanol; and |
| DCM | dichloromethane; | xvii) where an Isolute SCX-2 column is referred to, this means an "ion exchange" extraction cartridge for adsorption of basic compounds, i.e. a polypropylene tube containing a benzenesulphonic acid based strong cation exchange sorbent, used according to the manufacturers instructions obtained from International Sorbent Technologies Limited, Dyffryn Business Park, Hengeod, Mid Glamorgan, UK, CF82 7RJ;

xviii) where an Isolute amine column is referred to, this means an "ion exchange" extraction cartridge for adsorption of acidic compounds, i.e. a polypropylene tube containing a amino silane covalently bonded to a silica particle used according to the manufacturers instructions obtained from International Sorbent Technologies Limited, Dyffryn Business Park, Hengeod, Mid Glamorgan, UK, CF82 7RJ; and xix) where a Chemelut column is referred to, this means an extraction cartridge for removal of water, i.e. a polypropylene tube containing diatomaceous earth used according to the manufacturers instructions obtained from Varian, Harbor City, Calif., USA.

Example 1

4-(1-Ethyl-2-methylimidazol-5-yl)-2-{4-[N-(2-ethoxyethyl)sulphamoyl]anilino}pyrimidine Chlorosulphonic acid (280 μl, 4 mmol) was added dropwise to solution of 2-anilino-4-(1-ethyl-2-methylimidazol-5-yl)pyrimidine (Method 30; 279 mg, 1 mmol) in thionyl chloride (5 ml) cooled at 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of 2-ethoxyethylamine (356 mg, 4 mmol) and diethylmethylamine (1 ml, 15 mmol) in MeOH (3 ml) added. The mixture was stirred for 15 minutes and the volatiles were evaporated in vacuo. Water (20 ml) was added and extracted DCM (2×25 ml). DCM was dried and evaporated in vacuo. The residue was purified by flash chromatography on silica gel eluting with DCM:MeOH (100:0 increasing in polarity to 97:3) to yield a white foam. The white foam was dissolved in MeOH (3 ml) and treated with 1M HCl in ether (0.55 ml, 0.55 mmol). The solvent was evaporated in vacuo and the resultant solid triturated with ether, collected by filtration and dried-under vacuum at 60° C. to yield the title compound (128 mg, 47%) as a yellow solid. NMR: 1.05 (t, 3H), 1.30 (t, 3H), 2.76 (s, 3H), 2.88 (m, 2H), 3.32 (m, 4H), 4.76 (m, 2H), 7.37 (d, 1H), 7.52 (m, 1H), 7.73 (d, 2H), 7.90 (d, 2H), 8.43 (s, 1H), 8.65 (d, 1H), 10.14 (brs, 1H); m/z 431.

Examples 2-41

The following compounds were prepared by the procedure of Example 1 using the appropriate amine and 2-anilino4-(1-ethyl-2-methylimidazol-5-yl)pyrimidine (Method 30; Examples 2-11, 15, 16, 31-34), 2-anilino-4-(1,2-dimethylimidazol-5-yl)pyrimidine (Method 34; Examples 12-14), 2-anilino-4-(1-isopropyl-2-methylimidazol-5-yl)pyrimidine (Method 31; Examples 17, 18, 23-30 and 35-41), 2-anilino-4-[1-(2-methylpropyl)-2-methylimidazol-5-yl]pyrimidine (Method 38; Examples 19-20) and 2-anilino-4-(2-methyl-1-propylimidazol-5-yl)pyrimidine (Method 37; Examples 21-22).

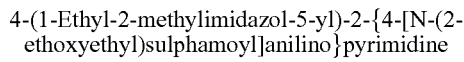

| Ex | $R^1$ | $R^2$ | NMR | M/z |
|---|---|---|---|---|
| $2^2$ | Et | ![NH-CH2CH2-pyridyl] | 1.28(t, 3H), 2.72(s, 3H), 3.18(m, 2H), 3.22(m, 2H), 4.74(q, 2H), 7.38(d, 1H), 7.70(d, 2H), 7.78 (t, 1H), 7.88(t, 4H), 8.42(t, 1H), 8.47(s, 1H), 8.68(d, 1H), 8.78(d, 1H), 10.19(s, 1H) | 464 |
| $3^3$ | Et | ![NH-C(CH3)2-C≡CH] | 1.28(t, 3H), 1.40(s, 6H), 2.71(s, 3H), 2.91(s, 1H), 4.72(q, 2H), 7.34(d, 1H), 7.74(d, 2H), 7.83 (d + m, 3H), 8.43(s, 1H), 8.68(d, 1H), 10.11(s, 1H) | 425 |
| $4^4$ | Et | ![NH-CH2-pyridyl-CF3] | 1.30(t, 3H), 2.75(s, 3H), 4.18(d, 2H), 5.78(q, 2H), 7.40(d, 1H), 7.72(d, 2H), 7.80(d, 1H), 7.88 (d, 2H), 7.94(d, 1H), 8.29(t, 1H), 8.48(s, 1H), 8.60(s, 1H), 8.70(d, 1H), 10.18(s, 1H) | 518 |

-continued

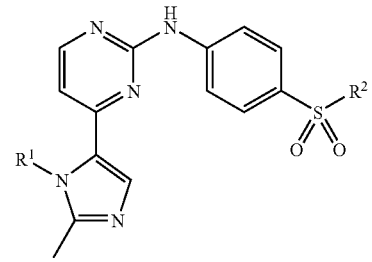

| Ex | R¹ | R² | NMR | M/z |
|---|---|---|---|---|
| 5[5] | Et | 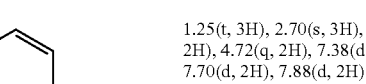 | 1.25(t, 3H), 2.49(s, 3H), 2.72(s, 3H), 2.95(m, 2H), 3.16(m, 2H), 4.73(q, 2H), 7.39(d, 1H), 7.75(d, 2H), 7.78(m, 1H), 7.90(d, 2H), 8.48(s, 1H), 8.67(d, 1H), 10.20(s, 1H) | 468 |
| 6[5] | Et | 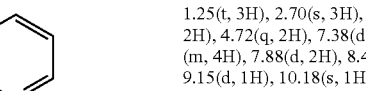 | 1.25(t, 3H), 2.70(s, 3H), 2.82(m, 2H), 3.04(m, 2H), 4.72(q, 2H), 7.38(d, 1H), 7.63(m, 2H), 7.70(d, 2H), 7.88(d, 2H), 8.01(d, 1H), 8.41(s, 1H), 8.60(m, 2H), 8.65(d, 1H), 10.15(s, 1H) | 464 |
| 7[6,14] | Et | 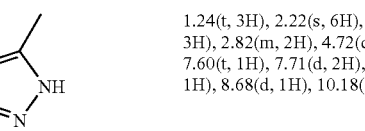 | 1.25(t, 3H), 2.70(s, 3H), 3.08(t, 2H), 3.18(q, 2H), 4.72(q, 2H), 7.38(d, 1H), 7.68(t, 1H), 7.70 (m, 4H), 7.88(d, 2H), 8.48(s, 1H), 8.68(d, 1H), 9.15(d, 1H), 10.18(s, 1H) | 465 |
| 8[7] | Et | 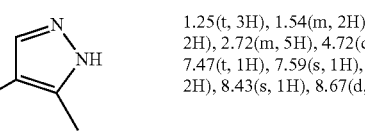 | 1.24(t, 3H), 2.22(s, 6H), 2.50(m, 2H), 2.71(s, 3H), 2.82(m, 2H), 4.72(q, 2H), 7.39(d, 1H), 7.60(t, 1H), 7.71(d, 2H), 7.89(d, 2H), 8.47(s, 1H), 8.68(d, 1H), 10.18(s, 1H) | 481 |
| 9[8] | Et | 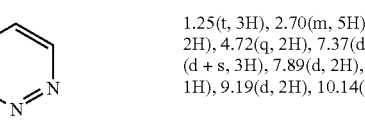 | 1.25(t, 3H), 1.54(m, 2H), 2.14(s, 3H), 2.34(t, 2H), 2.72(m, 5H), 4.72(q, 2H), 7.36(d, 1H), 7.47(t, 1H), 7.59(s, 1H), 7.71(d, 2H), 7.88(d, 2H), 8.43(s, 1H), 8.67(d, 1H), 10.12(s, 1H) | 481 |
| 10[9] | Et | 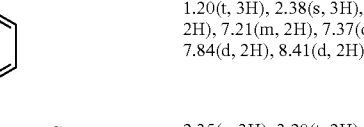 | 1.25(t, 3H), 2.70(m, 5H), 2.81(t, 2H), 3.08(m, 2H), 4.72(q, 2H), 7.37(d, 1H), 7.64(m 1H), 7.71 (d + s, 3H), 7.89(d, 2H), 8.45(s, 1H), 8.68(d, 1H), 9.19(d, 1H), 10.14(s, 1H) | 465 |
| 11 | Et | 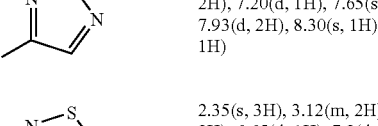 | 1.20(t, 3H), 2.38(s, 3H), 4.04(s, 2H), 4.58(q, 2H), 7.21(m, 2H), 7.37(d, 1H), 7.70(m, 4H), 7.84(d, 2H), 8.41(d, 2H), 9.80(s, 1H) | 450 |
| 12[10,12] | Me | 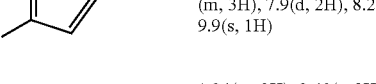 | 2.35(s, 3H), 3.20(t, 2H), 3.95(s, 3H), 4.35(t, 2H), 7.20(d, 1H), 7.65(s, 1H), 7.75(m, 3H), 7.93(d, 2H), 8.30(s, 1H), 8.45(d, 1H), 9.95(s, 1H) | 473 |
| 13[11] | Me | 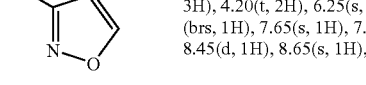 | 2.35(s, 3H), 3.12(m, 2H), 3.95(s, 3H), 4.25(t, 2H), 6.65(d, 1H), 7.2(d, 1H), 7.60(s, 1H), 7.7 (m, 3H), 7.9(d, 2H), 8.25(d, 1H), 8.82(d, 1H), 9.9(s, 1H) | 472 |
| 14[10,13] | Me |  | 1.84(m, 2H), 2.40(s, 3H), 2.90(t, 2H), 3.95(s, 3H), 4.20(t, 2H), 6.25(s, 1H), 7.25(d, 1H), 7.50 (brs, 1H), 7.65(s, 1H), 7.75(d, 2H), 7.95(d, 2H), 8.45(d, 1H), 8.65(s, 1H), 9.95(s, 1H) | 468 (M − H)⁻ |

-continued
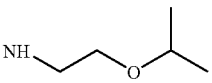
| Ex | R¹ | R² | NMR | M/z |
|---|---|---|---|---|
| 15 | Et | 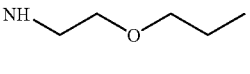 | 1.03(d, 6H), 1.28(t, 3H), 2.71(s, 3H), 2.86(q, 2H), 3.31(t, 2H), 3.46(m, 1H), 4.74(q, 2H), 7.35 (d, 1H), 7.49(t, 1H), 7.72(d, 2H), 7.88(d, 2H), 8.42(s, 1H), 8.65(d, 1H), 10.12(s, 1H) | 445 |
| 16 | Et | 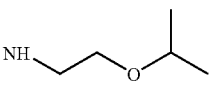 | 0.81(t, 3H), 1.25(t, 3H), 1.44(m, 2H), 2.70(s, 3H), 2.88(q, 2H), 3.23(t, 2H), 3.34(t, 2H), 4.72 (q, 2H), 7.35(d, 1H), 7.49(t, 1H), 7.72(d, 2H), 7.88(d, 2H), 8.42(s, 1H), 8.65(d, 1H), 10.12(s, 1H) | 445 |
| 17 | i-Pr | 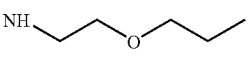 | 1.01(d, 6H), 1.50(d, 6H), 2.79(s, 3H), 2.84(q, 2H), 3.30(t, 2H), 3.50(m, 1H), 5.56(m, 1H), 7.24(d, 1H), 7.49(t, 1H), 7.70(d, 2H), 7.88(d, 2H), 8.42(s, 1H), 8.68(d, 1H), 10.17(s, 1H) | 459 |
| 18 | i-Pr | 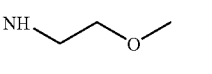 | 0.88(t, 3H), 1.42(quin, 2H), 1.51(d, 6H), 2.77 (s, 3H), 2.87(q, 2H), 3.23(t, 2H), 5.55(m, 1H), 7.24(d, 1H), 7.52(t, 1H), 7.70(d, 2H), 7.88(d, 2H), 8.42(s, 1H), 8.68(d, 1H), 10.17(s, 1H) | 459 |
| 19 | i-Bu | 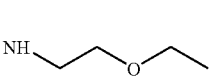 | (400 MHz) 0.69(d, 6H), 1.78(m, 1H), 2.69(s, 3H), 2.88(m, 2H), 3.20(s, 3H), 3.32(m, 2H), 4.60(d, 2H), 7.36(d, 1H), 7.56(t, 1H), 7.73(d, 2H), 7.73(d, 2H), 8.42(s, 1H), 8.68(d, 1H), 10.20(s, 1H) | 445 |
| 20 | i-Bu |  | (400 MHz) 0.72(d, 6H), 1.06(t, 3H), 1.78(m, 1H), 2.72(s, 3H), 2.89(q, 2H), 3.36(m, 4H), 4.60(d, 2H), 7.36(d, 1H), 7.55(t, 1H), 7.75(d, 2H), 7.80(d, 2H), 8.43(s, 1H), 8.68(d, 1H), 10.20(s, 1H) | 459 |
| 21 | n-Pr |  | 0.70(t, 3H), 1.03(t, 3H), 1.60(m, 2H), 2.73(s, 3H), 2.86(t, 2.04), 3.32(m, 4H), 4.69(t, 2H), 7.36(d, 1H), 7.57(br s, 1H), 7.73(d, 2H), 7.88 (d, 2H), 8.47(s, 1H), 8.64(d, 1H), 10.25(s, 1H) | 445 |
| 22 | n-Pr | 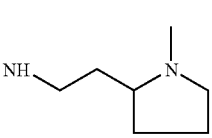 | 0.70(t, 3H), 1.60(m, 2H), 2.72(s, 3H), 2.21(m, 2H), 3.16(m, 3H), 3.30(t, 2H), 4.68(t, 2H), 7.35 (d, 1H), 7.56(br s, 1H), 7.73(d, 2H), 7.87(d, 2H), 8.45(s, 1H), 8.65(d, 1H), 10.19(s, 1H) | 431 |
| 23 | i-Pr | 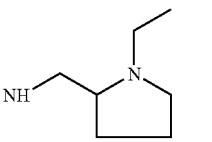 |  | 484 |
| 24 | i-Pr | 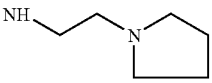 |  | 484 |
| 25 | i-Pr |  |  | 470 |

| Ex | R¹ | R² | NMR | M/z |
|---|---|---|---|---|
| 26 | i-Pr |  | | 486 |
| 27 | i-Pr |  | | 500 |
| 28 | i-Pr |  | | 484 |
| 29 | i-Pr |  | 1.48(d, 6H), 2.50(s, 3H), 2.78(m, 2H), 3.35(m, 2H), 4.62(t, 1H), 5.68(sept, 1H), 7.14(d, 1H), 7.38(br s, 1H), 7.48(s, 1H), 7.70(d, 2H), 7.89(d, 2H), 8.47(d, 1H), 9.89(s, 1H) | 417 |
| 30 | i-Pr |  | 1.55(m, 8H), 2.78(m, 5H), 3.18(s, 3H), 3.36(m, 6H), 5.58(m, 1H), 7.25(d, 1H), 7.41(t, 1H), 7.69(d, 2H), 7.89(d, 2H), 8.19(s, 1H), 8.68(d, 1H), 10.19(s, 1H) | 488 |
| 31 | Et |  | 1.22(t, 3H), 2.75(s, 3H), 3.10(t, 2H), 3.96(t, 2H), 4.74(m, 2H), 6.85(m, 3H), 7.22(t, 2H), 7.38(d, 1H), 7.76(d, 2H), 7.85(m, 1H), 7.92(d, 2H), 8.49(s, 1H), 8.63(d, 1H), 10.24(s, 1H) | 479 |
| 32 | Et |  | 1.26(t, 3H), 2.72(s, 3H), 3.08(m, 2H), 3.65(s, 3H), 3.88(t, 2H), 4.73(m, 2H), 6.78(m, 4H), 7.37(d, 1H), 7.75(m, 3H), 7.89(d, 2H), 8.47(s, 1H), 8.65(d, 1H), 10.18(s, 1H) | 509 |
| 33 | Et |  | 1.26(t, 3H), 2.93(s, 3H), 1.93(3.08), 3.73(s, 3H), 3.95(t, 2H), 4.74(m, 2H), 6.88(m, 4H), 7.38(d, 1H), 7.77(d, 1H), 7.91(d, 2H), 8.47(s, 1H), 8.65(d, 1H), 10.20(s, 1H) | 509 |
| 34 | Et |  | 1.19(t, 3H), 2.40(s, 3H), 2.99(q, 2H), 3.65(t, 2H), 3.95(dd, 1H), 4.13(dd, 1H), 4.57(m, 2H), 6.43(dd, 1H), 7.21(d, 1H), 7.60(t, 1H), 7.68(s, 1H), 7.71(d, 2H), 7.89(d, 2H), 8.42(d, 1H), 9.81(s, 1H) | 429 |
| 35 | i-Pr |  | 1.05(s, 9H), 1.52(m, 8H), 2.06(m, 2H), 2.80(s, 3H), 3.24(t, 2H), 5.49(m, 1H), 7.25(d, 1H), 7.39(br s, 1H), 7.70(d, 2H), 7.89(d, 2H), 8.21(s, 1H), 8.68(d, 1H), 10.20(s, 1H) | 487 |
| 36 | i-Pr | | 1.04(t, 3H), 1.54(m, 8H), 2.80(m, 5H), 3.38(m, 12H), 5.58(m, 1H), 7.25(d, 1H), 7.41(br s, 1H), 7.70(d, 2H), 7.89(d, 2H), 8.21(s, 1H), 10.20(s, 1H) | 547 |

-continued

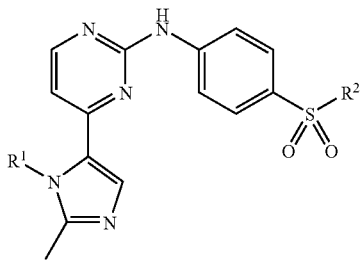

| Ex | R¹ | R² | NMR | M/z |
|---|---|---|---|---|
| 37 | i-Pr | NH-CH₂CH₂-N(CH₃)₂ | | 444 |
| 38 | i-Pr | NH-CH₂CH₂-N(Et)₂ | | 472 |
| 39 | i-Pr | NH-CH₂-C(O)-O-tBu | 1.30(s, 9H), 1.47(d, 6H), 3.53(d, 2H), 5.65(m, 1H), 7.14(d, 1H), 7.44(s, 1H), 7.67(d, 2H), 7.85 (m, 3H), 8.45(d, 1H), 9.86(s, 1H) | 487 |
| 40 | i-Pr | 4-NH-piperidine-N-benzyl | | 546 |
| 41 | i-Pr | NH-CH₂-C(O)-O-Me | 1.46(d, 6H), 3.26(s, 3H), 3.52(s, 3H), 3.66(s, 2H), 5.66(m, 1H), 7.14(d, 1H), 7.44(s, 1H), 7.68(d, 2H), 7.87(d, 2H), 7.96(s, 1H), 8.45(d, 1H), 9.87(s, 1H) | 445 |

[1] Isolated as Free Base

[2] Purified by flash silica chromatography DCM:MeOH (96:4)

[3] Purified by flash silica chromatography DCM:MeOH (98:2 increasing in polarity to 96:4)

[4] Purified by flash silica chromatography DCM:MeOH (95:5)

[5] Purified by flash silica chromatography DCM:MeOH (98:2 increasing in polarity to 90:10). The residue was further purified by flash alumina chromatography DCM:MeOH (90:10)

[6] Water (15 ml) added, basified with saturated sodium bicarbonate solution to pH 8, extracted into EtOAc (5 × 15 ml). Organics were washed with brine (10 ml), dried evaporated.

[7] Purified by flash alumina chromatography DCM:MeOH (96:4 increasing in polarity to 80:20).

[8] Purified by flash alumina chromatography DCM:MeOH (98:2 increasing in polarity to 90:10).

[9] Purified by flash alumina chromatography DCM:MeOH (96:4 increasing in polarity to 90:10). The residue was further purified by flash silica chromatography (DCM:MeOH (97:3)): ammonia (100:0 increasing in polarity to 99:1)

[10] Purified by Isolute amine column

[11] Recrystallised from MeOH

[12] Starting amine - Method 78

[13] Starting amine - Method 79

[14] Starting amine - JACS 1950, 72, 3539

Examples 42-45

The following compounds were prepared by the procedure of Example 1 using the appropriate amine and 2-anilino-4-(1-propylimidazol-5-yl)pyrimidine (Method 36; Examples 42, 44 and 45) and 2-anilino-4-(1-ethylimidazol-5-yl)pyrimidine (Method 32; Example 43).

| Ex | R¹ | R² | NMR | M/z |
|---|---|---|---|---|
| 42 | n-Pr | 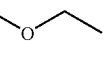 | 0.74(t, 3H), 1.70(m, 2H), 2.86(q, 2H), 3.15 (s, 3H), 3.29(m, 2H), 4.69(t, 2H), 7.40(d, 1H), 7.55(t, 1H), 7.72(d, 2H), 7.87(d, 2H), 8.50(s, 1H), 8.67(d, 1H), 9.28(s, 1H), 10.17 (s, 1H) | 417 |
| 43 | Et | 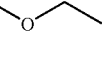 | 1.04(t, 3H), 1.38(t, 3H), 2.84(m, 2H), 3.30 (m, 4H), 4.74(q, 2H), 7.40(d, 1H), 7.55(m, 1H), 7.74(d, 2H), 7.89(d, 2H), 8.55(s, 1H), 8.68(d, 1H), 9.40(s, 1H), 10.20(s, 1H) | 417 |
| 44 | n-Pr | | 0.72(t, 3H), 1.05(t, 3H), 1.70(sext, 2H), 2.85 (q, 2H), 3.31(q, 4H), 4.69(t, 2H), 7.38(d, 1H), 7.51(t, 1H), 7.71(d, 2H), 7.85(d, 2H), 8.47(s, 2H), 8.66(d, 1H), 9.25(s, 1H), 10.16 (s, 1H) | 431 |
| 45 | n-Pr | 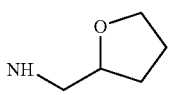 | 0.73(t, 3H), 1.50(m, 2H), 1.73(m, 4H), 2.73 (m, 2H), 3.55(q, 1H), 3.67(q, 1H), 3.80(quin, 1H), 4.70(t, 1H), 7.38(d, 1H), 7.55(t, 1H), 7.71(d, 2H), 7.85(d, 2H), 8.50(s, 2H), 8.67 (d, 1H), 9.30(s, 1H), 10.17(s, 1H) | 443 |

Example 46

4-(1-Ethylimidazol-5-yl)-2-{4-[N-(cyclopropyl)sulphamoyl]anilino}pyrimidine

Chlorosulphonic acid (250 μl, 3.6 mmol) was added dropwise to solution of 2-anilino-4-(1-ethylimidazol-5-yl)pyrimidine (Method 32; 250 mg, 0.9 mmol) in thionyl chloride (5 ml) cooled at 0° C. and the mixture stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of cyclopropylamine (1 ml, 13.5 mmol) in MeOH (4ml) added. The mixture was stirred for 15 minutes and the volatiles were evaporated in vacuo. Water (20ml) was added and the resultant solid was washed with water (2×10 ml), ether (2×10 ml) and dried under vacuum at 60° C. for 18 hr. The resultant solid was dissolved in MeOH (4 ml) and treated with 1M HCl in ether (0.62 ml, 0.62 mmol). The solvent was evaporated in vacuo and the resultant solid triturated with ether, collected by filtration and dried under vacuum at 60° C. to yield the title compound (220 mg, 56%) as a golden solid. NMR: 0.34 (m, 2H), 0.52 (m, 2H), 1.52 (t, 3H), 2.21 (m, 1H), 4.77 (q, 2H), 7.43 (d, 1H), 7.74 (m, 3H), 7.93 (d, 2H), 8.54 (s, 1H), 8.72 (d, 1H), 9.41 (s, 1H), 10.20 (brs, 1H); m/z 385.

Examples 47-64

The following compounds were prepared by the procedure of Example 46 using the appropriate starting materials.

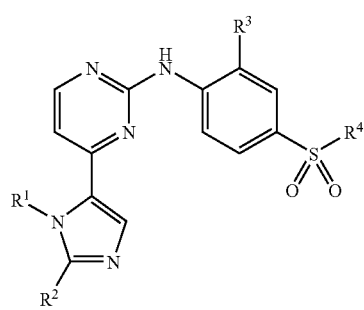

| Ex | R$^1$ | R$^2$ | R$^3$ | R$^4$ | NMR | M/z | SM |
|---|---|---|---|---|---|---|---|
| 47[1] | Me | Me | H | NH-CH$_2$CH$_2$-O-Et | 1.04(t, 3H), 2.40(s, 3H), 2.88(q, 2H), 3.32(m, 4H), 3.96(s, 3H), 7.18(d, H), 7.44(t, 1H), 7.68(s, 1H), 7.70(d, 2H), 7.92(d, 2H), 8.44(d, 1H), 9.92(s, 1H) | 417 | Meth 34 |
| 48[1] | Me | Me | H | NH-t-Bu | 1.15(s, 9H), 2.38(s, 3H), 3.97(s, 3H), 7.19(d, 1H), 7.24(s, 1H), 7.63(s, 1H), 7.76(d, 2H), 7.88(d, 2H), 8.42(d, 1H), 9.87(s, 1H) | 401 | Meth 34 |
| 49[1,2] | Me | Me | H | NH-C(Me)(Et)- | 0.74(t, 3H), 1.05(s, 3H), 1.45(q, 2H), 2.40(s, 3H), 3.95(s, 3H), 7.22-7.18(m, 2H), 7.65(s, 1H), 7.70(d, 2H), 7.91(d, 2H), 8.45(d, 1H), 9.90(s, 1H) | 415 | Meth 34 |
| 50[1] | Me | Me | H | NH-CH$_2$CH$_2$-pyrazole | 2.39(s, 3H), 3.12(q, 2H), 3.96(s, 3H), 4.15(t, 2H), 6.19(s, 1H), 7.20(d, 1H), 7.40(s, 1H), 7.58(t, 1H), 7.68-7.62(m, 4H), 7.92(d, 2H), 8.43(d, 1H), 9.92(s, 1H) | 439 | Meth 34 |
| 51[1] | Me | Me | H | NH-CH(Me)-CH$_2$OH | 0.89(d, 3H), 2.40(s, 3H), 3.08(t, 2H), 3.96(s, 3H), 4.60(s, 1H), 7.22(dd, 2H), 7.74(m, 3H), 7.92 (d, 2H), 8.43(d, 1H), 9.90(s, 1H) | | Meth 34 |
| 52[1,3] | Me | Me | H | NH-CH(CH$_2$OH)$_2$ | 2.39(s, 3H), 3.08-3.00(m, 2H), 3.32-3.22(m, 2H), 3.60-3.44(m, 1H), 3.98(s, 3H), 4.50(t, 2H), 7.14(d, 1H), 7.20(d, 1H), 7.64(s, 1H), 7.73(d, 2H), 7.90(d, 2H), 8.44(d, 1H), 9.89(s, 1H) | 419 | Meth 34 |
| 53[1] | Me | Me | H | NH-CH(Me)-CH$_2$OMe | 0.9(d, 3H), 2.38(s, 3H), 3.25-3.06 (m, 6H), 3.97(s, 3H), 7.20(d, 1H), 7.40(d, 1H), 7.64(s, 1H), 7.72(d, 2H), 7.92(d, 2H), 8.43(d, 1H), 9.89(s, 1H) | 417 | Meth 34 |
| 54 | i-Pr | H | H | NH-cyclopropyl | 0.34(m, 2H), 0.52(m, 2H), 1.52 (d, 6H), 2.21(m, 1H), 5.81(m, 1H), 7.43(d, 1H), 7.74(m, 3H), 7.92(d, 2H), 8.52(s, 1H), 8.71(d, 1H), 9.54(s, 1H), 10.20(brs, 1H) | 399 | Meth 33 |
| 55 | i-Pr | H | H | NH-CH$_2$CH$_2$-OMe | 1.52(d, 6H), 2.86(m, 2H), 3.16(s, 3H), 3.28(m, 2H), 5.79(m, 1H), 7.38(d, 1H), 7.55(m, 1H), 7.72 (d, 2H), 7.86(d, 2H), 8.52(s, 1H), 8.68(d, 1H), 9.58(s, 1H), 10.20 (brs, 1H) | 417 | Meth 33 |

| Ex | R¹ | R² | R³ | R⁴ | NMR | M/z | SM |
|---|---|---|---|---|---|---|---|
| 56 | i-Pr | H | H | ![NH-CH2-tetrahydrofuran] | 1.50(m, 7H), 1.75(m, 3H), 2.86 (m, 2H), 3.55(m, 1H), 3.66(m, 1H), 3.78(m, 1H), 5.80(m, 1H), 7.38(d, 1H), 7.53(m, 1H), 7.72 (d, 2H), 7.86(d, 2H), 8.52(s, 1H), 8.68(d, 1H), 9.58(s, 1H), 10.19 (brs, 1H) | 443 | Meth 33 |
| 57[4] | i-Pr | Me | H | NH-iPr | 1.52(d, 6H), 2.39(s, 3H), 3.18(s, 3H), 2.79(s, 3H), 5.58(m, 1H), 7.28(d, 1H), 7.30(br t, 1H), 7.69 (d, 2H), 7.89(d, 2H), 8.20(s, 1H) 8.70(d, 1H), 10.20(s, 1H), 15.00 (v brs, 0.7H) | 387 | Meth 31 |
| 58[5] | Et | H | H | NH-CH2CH2-OMe | 1.40(t, 3H). 2.90(q, 2H), 3.15(s, 3H), 3.3(t, 2H), 4.75(q, 2H), 7.4 (d, 1H), 7.5(t, 1H), 7.73(d, 2H), 7.9(d, 2H), 8.5(s, 1H), 8.7(d, 1H), 9.30(s, 1H) | 403 | Meth 32 |
| 59[1,6] | Me | Me | H | NH-C(Me)2-CH2OH | 1.00(s, 6H), 2.37(s, 3H), 3.17(d, 2H), 3.95(s, 3H), 4.68(t, 1H), 7.0 (s, 1H), 7.17(d, 1H), 7.63(s, 1H), 7.73(d, 2H), 7.87(d, 2H), 8.43(d, 1H), 9.87(s, 1H) | 417 | Meth 34 |
| 60[1] | Me | Me | F | NH-CH2CH2-OMe | 2.37(s, 3H), 2.93(t, 2H), 3.17(s, 3H), 3.28(t, 2H), 3.84(s, 3H), 7.2 (d, 1H), 7.6(m, 3H), 7.67(s, 1H), 8.08(t, 1H), 8.38(d, 1H), 9.4(s, 1H) | 421 | Meth 35 |
| 61[1,5] | Me | Me | F | NH₂ | 2.35(s, 3H), 3.85(s, 3H), 7.2(d, 1H), 7.35(s, 2H), 7.62(m, 3H), 8.07(t, 1H), 8.4(d, 1H), 9.35(s, 1H) | 363 | Meth 35 |
| 62 | i-Pr | Me | H | NH₂ | 1.47(d, 6H), 2.49(s, 3H), 5.68 (sept, 1H), 7.13(m, 3H), 7.43(s, 1H), 7.72(d, 2H), 7.85(d, 2H), 8.44(d, 1H), 9.81(s, 1H) | 373 | Meth 31 |
| 63 | n-Pr | H | H | NH-cyclopropyl | 0.38(m, 2H), 0.43(m, 2H), 0.75 (t, 3H), 1.70(m, 2H), 2.10(s, 1H), 4.71(t, 2H), 7.40(d, 1H), 7.74(d, 3H), 7.92(d, 2H), 8.51(s, 1H), 8.69(d, 1H), 9.30(s, 1H), 10.20 (s, 1H) | 399 | Meth 36 |
| 64 | n-Pr | Me | H | NH-cyclopropyl | 0.37(m, 2H), 0.46(m, 2H), 0.69 (m, 3H), 1.61(m, 2H), 2.11(m, 1H), 2.73(s, 3H), 4.69(t, 2H), 7.36(d, 1H), 7.74(m, 3H), 7.91 (d, 2H), 8.47(s, 1H), 8.66(d, 1H), 10.25(s, 1H) | 413 | Meth 37 |

[1] Isolated as free base
[2] Purified by flash silica chromatography DCM:MeOH (90:10)
[3] Purified by flash silica chromatography DCM:MeOH (85:15)
[4] Purified by flash silica chromatography DCM:MeOH (95:5 increasing in polarity to 90:10)
[5] Purified by Isolute amine column
[6] i-PrOH used in place of MeOH

Example 65

2-{4-[N-(1-Morpholino-2-methylprop-2-yl)sulphamoyl]anilino}-4-(1,2-dimethylimidazol-5-yl)pyrimidine 2-[4-(2,2-Dimethylaziridin-1-ylsulphonyl)anilino]-4-(1,2-dimethylimidazol-5-yl)pyrimidine (Example 47; 200 mg, 0.502 mmol) was dissolved on warming in morpholine (4.7 ml, excess) and stirred at room temperature for 3 days. The excess morpholine was removed in vacuo and the residue dissolved in EtOAc (40 ml) and washed with water (3×40 ml), dried the solvent evaporated in vacuo. The crude product was triturated with ether filtered washed with ether and air-dried to give the title compound (200 mg, 82%) as a white solid. NMR 1.03 (s, 6H), 2.27 (s, 2H), 2.38 (s, 3H), 2.47 (m, 4H), 3.52 (m, 4H), 3.95 (s, 3H), 7.05 (s, 1H), 7.2 (d, 1H), 7.63 (s, 1H), 7.72 (d, 2H), 7.88 (d, 2H), 8.43 (d, 1H), 9.86 (s, 1H); m/z 486.

Example 66

Example 66 was prepared by the procedure of Example 65 using the appropriate starting material

| Ex | Compound | NMR | m/z |
|---|---|---|---|
| 66[2] | 2-{4-[N-(1-Pyrrolidin-1-yl-2-methylprop-2-yl)sulphamoyl]anilino}-4-(1,2-dimethylimidazol-5-yl)pyrimidine | 1.03(s, 6H), 1.62(m, 4H), 2.35(s, 3H), 2.42(s, 2H), 2.53(m, 4H), 3.93(s, 3H), 6.95(s, 1H), 7.18(d, 1H), 7.63(s, 1H), 7.73(d, 2H), 7.87(d, 2H), 8.43(d, 1H), 9.86(s, 1H) | 470 |

Example 67

4-(1-Isopropyl-2-methylimidazol-5-yl)-2-{4-[N-(2-ethoxyethyl)sulphamoyl]anilino}pyrimidine To a stirred solution of 2-amino-4-(1-isopropyl-2-methylimidazol-5-yl)pyrimidine (Method 39; 163 mg, 0.75 mmol), N-(2-ethoxyethyl)-4-iodobenzenesulphonamide (Method 44; 400 mg, 1.13 mmol), tris(dibenzylideneacetone)dipalladium (0) (35 mg, 0.038 mmol) and 2,2'-bis(diphenylphosphino)-1,1'-binaphthyl (47 mg, 0.076 mmol) in dioxane (10 ml) was added sodium t-butoxide (258 mg, 2.69 mmol) and the mixture heated at 80° C. overnight. The reaction was cooled to room temperature and MeOH 105 ml) was added and the mixture poured onto an Isolute SCX-2 column, eluted first with MeOH (10×30 ml) and the product was then eluted with 5% methanolic ammonia (10×30 ml). The solvent was removed by evaporation and the residue purified by flash chromatography on silica gel eluting with DCM/MeOH (100:0 increasing in polarity to 97:3) to yield a foam which was dissolved in MeOH (2 ml) and treated with 1N HCl in ether (350 µl, 0.35 mmol) for 5 minutes. Solvent was evaporated in vacuo to yield a yellow foam which was triturated with ether to yield after filtration the title compound as a yellow solid (141 mg, 39%) NMR: 1.05 (t, 3H), 1.53 (d, 6H), 2.80 (s, 3H), 2.85 (q, 2H), 3.32 (m, 4H), 5.58 (m, 1H), 7.21 (d, 1H), 7.52 (t, 1H), 7.73 (d, 2H), 7.86 (d, 2H), 8.39 (s, 1H), 8.68 (d, 1H), 10.18 (brs, 1H); m/z 445.

Examples 68-76

The following compounds were prepared by the procedure of Example 67 using the appropriate starting materials.

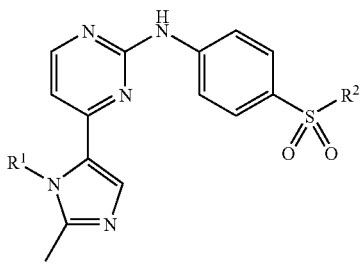

| Ex | R[1] | R[2] | NMR | M/z | SM |
|---|---|---|---|---|---|
| 68[2] | i-Pr | MeO(CH₂)₃— | 1.57(d, 6H), 1.78(m, 2H), 2.81(s, 3H), 3.18(s, 3H), 3.28(m, 2H), 3.36(m, 2H), 5.58(m, 1H), 7.30(d, 1H), 7.82(d, 2H), 7.99(d, 2H), 8.22(s, 1H), 8.78(d, 1H), 10.32(s, 1H) | 434 | Meth 39 Meth 69 |
| 69[3] | i-Pr | Me | 1.52(d, 6H), 2.79(s, 3H), 3.14(s, 3H), 5.56(m, 1H), 7.28(d, 1H), 7.83(d, 2H), 7.96(d, 2H), 8.20(s, 1H), 8.71(d, 1H), 10.28(s, 1H) | 372 | Meth 39[7] |

-continued

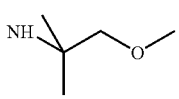

| Ex | R¹ | R² | NMR | M/z | SM |
|---|---|---|---|---|---|
| 70[4] | i-Pr | Me₂N(CH₂)₃— | 1.52(d, 6H), 1.98(m, 2H), 2.68(s, 9H), 3.09(t, 2H), 3.38(t, 2H), 5.58 (m, 1H), 7.25(d, 1H), 7.81(d, 2H), 7.98(s, 1H), 7.99(d, 2H), 8.65(d, 1H), 10.25(s, 1H), 10.53(brs, 0.7H) | 443 | Meth 39 Meth 65 |
| 71[5] | i-Pr | n-Bu | 0.82(t, 3H), 1.30(m, 2H), 1.49(m, 2H), 1.51(d, 6H), 2.80(s, 3H), 3.22 (m, 2H), 5.54(m, 1H), 7.29(d, 1H), 7.79(d, 2H), 7.96(d, 2H), 8.20(s, 1H), 8.71(d, 1H), 10.29(s, 1H), 15.10 (v brs, 0.7H) | 414 | Meth 39 Meth 67 |
| 72[6] | i-Pr | CF₃—(CH₂)₂— | 1.52(d, 6H), 2.58(m, 2H), 2.80(s, 3H), 3.55(m, 2H), 5.56(m, 1H), 7.30 (d, 1H), 7.89(d, 2H), 8.00(d, 2H), 8.22(s, 1H), 8.76(d, 1H), 10.36(s, 1H), 15.50(v brs, 0.7H) | 454 | Meth 39 Meth 66 |
| 73[1] | Me | 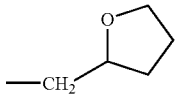 | 1.05(s, 6H), 2.37(s, 3H), 3.1(s, 3H), 3.95(s, 3H), 7.18(d, 1H), 7.22(s, 1H), 7.63(s, 1H), 7.76(d, 2H), 7.88 (d, 2H), 8.43(d, 1H), 9.86(s, 1H) | 431 | Meth 40 Meth 43 |
| 74 | i-Pr |  | 1.54(d, 6H), 1.75(m, 2H), 1.93(m, 2H), 2.79(s, 3H), 3.45(t, 2H), 3.52 (m, 1H), 3.60(q, 1H), 4.04(quin, 1H), 5.57(sept, 1H), 7.29(d, 2H), 7.79(d, 2H), 7.94(d, 2H), 8.21(s, 1H), 8.72 (d, 1H), 10.29(s, 1H) | 442 | Meth 39 Meth 48 |
| 75 | i-Pr | EtO(CH₂)₃— | 1.06(t, 3H), 1.55(d, 6H), 1.76(m, 2H), 2.82(s, 3H), 3.25(m, 2H), 3.34 (m, 4H), 5.59(sept, 1H), 7.30(d, 1H), 7.82(d, 2H), 7.99(d, 2H), 8.21(s, 1H), 8.73(d, 1H), 10.32(s, 1H) | 444 | Meth 39 Meth 49 |
| 76 | i-Pr | (cyclopropylmethoxyethylamino) | 0.11(m, 2H), 0.40(m, 2H), 0.91(m, 1H), 1.53(d, 6H), 1.80(s, 3H), 2.87 (m, 2H), 3.14(d, 2H), 3.35(t, 2H), 5.57(m, 1H), 7.25(d, 1H), 7.55(t, 1H), 7.72(d, 2H), 7.88(d, 2H), 8.20 (s, 1H), 8.69(d, 1H), 10.18(s, 1H) | 471 | Meth 39 Meth 47 |

[1] Isolated as free base
[2] Purified by flash silica chromatography (DCM:MeOH 98:2): ammonia (100:0 increasing in polarity to 99:1) Residues was further purified by flash silica chromatography DCM:MeOH (96:4)
[3] Purified by flash silica chromatography DCM:MeOH (98:2 increasing in polarity to 90:10)
[4] Purified by flash silica chromatography DCM:MeOH/NH₃ (1% v/v) (95:5 increasing in polarity to 85:15)
[5] Purified by flash silica chromatography DCM:MeOH (97:3 increasing in polarity to 95:5)
[6] Purified by flash silica chromatography DCM:MeOH (95:5)
[7] The other intermediate was 4-bromo-phenyl methyl sulphone (commercially available)

Example 77

4-(1,2-Dimethylimidazol-5-yl)-2-{4-[N-(1,3-dimethoxyprop-2-yl)sulphamoyl]anilino}pyrimidine Chlorosulphonic acid (230 μl, 3.31 mmol) was added to a solution of the 2-anilino-4-(1,2-dimethylimidazol-5-yl)pyrimidine (Method 34; 300 mg, 1.12 mmol) in thionyl chloride (6 ml) at 5° C. The mixture was stirred at 5° C. for 30 minutes, room temperature for 1 hour and heated at reflux for 1.5 hour. The mixture was allowed to cool to room temperature and a solution of excess 1,3-dimethoxy-2-aminopropane (Method 59) in ethanol (20 ml) and dimethylethylamine (0.5 ml) were added to the residue, and the mixture stirred at room temperature for 18 hours. The volatiles were removed by evaporation. The residue was triturated with water and the solid product collected by filtration and dried under vacuum at 60° C. The residue was purified by flash silica chromatography DCM: MeOH (95:5) to give the title compound. NMR: 2.40 (s, 3H), 3.10 (s, 6H), 3.20(d, 4H), 3.32-3.28 (m, 1H), 3.98 (s, 3H), 7.20 (d, 1H), 7.55 (d, 1H), 7.65 (s, 2H), 7.74 (d, 2H), 7.90 (d, 2H), 8.44 (d, 2H), 9.89 (s, 1H); m/z 447

Examples 78-80

The following compounds were prepared by the procedure of Example 77 using the appropriate amine.

Example 81

2-{4-[N-(1-Methylthio-2-methylprop-2-yl)sulphamoyl]anilino}-4-(1,2-dimethylimidazol-5-yl)pyrimidine 2-[4-(2,2-Dimethylaziridin-1-ylsulphonyl)anilino]-4-(1,2-dimethylimidazol-5-yl)pyrimidine (Example 47; 200 mg, 0.50 mmol) was dissolved in dry DMF (10 ml) and NaSMe (176 mg, 2.51 mmol) added as a solid. The mixture was stirred under inert gas at room temperature overnight. Acetic acid (150 μl, 2.62 mmol) was added and volatiles were evaporated vacuo. The residue was treated with EtOAc (30 ml)/water (30 ml) and the suspension filtered and the solid washed with water and dried. The crude product was triturated with MeOH, filtered, washed with MeOH and dried to give the title compound (205 mg, 75%) as a white solid; NMR 1.10 (s, 6H), 2.06 (s, 3H), 2.37 (s, 3H), 2.62 (2, 2H), 3.95 (s, 3H), 7.2 (d, 1H), 7.35 (s, 1H), 7.63 (s, 1H), 7.73 (d, 2H), 7.87 (d, 2H), 8.43 (d, 1H), 9.86 (s, 1H), m/z 447.

Example 82

The following compound was prepared by the procedure of Method 80 using Method 72 as a starting material.

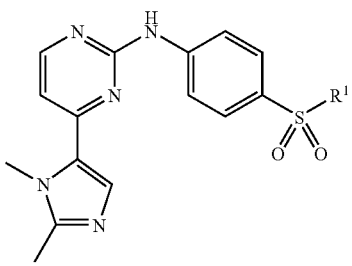

| Ex | R¹ | NMR | M/z |
|---|---|---|---|
| 78[2] | NH-CH(CH₃)-CH₂-O-Et | 0.9(d, 3H), 1.0(t, 3H), 2.38(s, 3H), 3.14-3.08(m, 1H), 3.31-3.20(m, 4H), 3.97(s, 3H), 7.19(d, 1H), 7.38(d, 1H), 7.63(s, 1H), 7.7(d, 2H), 7.90(d, 2H), 8.43(d, 1H), 9.91(s, 1H) | 431 |
| 79[3,1] | NH-cyclopropyl-CH₃ | 0.02(t, 2H), 0.25(t, 2H), 0.75(s, 3H), 2.08(s, 3H), 3.64(s, 3H), 6.90(d, 2H), 7.31(s, 1H), 7.38(d, 2H), 7.45(s, 1H), 7.60(d, 2H), 8.10(d, 1H), 9.60(s, 1H) | 399 |
| 80[4] | NH-CH(CH₃)-CH₂-O-CH₂CH₃ | 0.79(t, 3H), 0.89(d, 3H), 1.40(q, 2H), 2.39(s, 3H)., 3.12-3.08(m, 1H), 3.23-3.18(m, 4H), 3.96(s, 3H), 7.20(d, 2H), 7.40(d, 1H), 7.64(s, 1H), 7.75(d, 2H), 7.92(d, 2H), 8.41 (d, 1H), 9.90(s, 1H) | 445 |

[1]Starting Material: Method 52
[2]Purified by flash silica chromatography DCM:MeOH (96:4); starting material: Method 60
[3]Purified by flash silica chromatography DCM:MeOH (93:7)
[4]Purified by flash silica chromatography DCM:MeOH (97:3); starting material: Method 61

| Ex | Compound | NMR | m/z |
|---|---|---|---|
| 82 | 5-Bromo-4-(1-isopropyl-2-methylimidazol-5-yl)-2-{4-[N-(2-methoxyethyl)sulphamoyl]anilino}pyrimidine | 1.44(d, 6H), 2.78(s, 3H), 2.87(q, 2H), 3.15(s, 3H), 3.28(t, 2H), 5.76(m, 1H), 7.59(t, 1H), 7.71(d, 2H), 7.87(d, 2H), 8.01(s, 1H), 8.96(s, 1H), 10.52(s, 1H), 14.50(v brs, 0.7H) | 509 |

Example 83

5-Cyano-4-(1-ethyl-2-methylimidazol-5-yl)-2-{4-[N-(2-methoxyethyl)sulphamoyl]anilino}pyrimidine A suspension of 5-bromo-4-(1-ethyl-2-methylimidazol-5-yl)-2-{4-[N-(2-methoxyethyl)sulphamoyl]anilino}pyrimidine (Method 80; 0.35 g, 0.70 mmol), zinc cyanide (0.05 g, 0.42 mmol), tris(dibenzylideneacetone)dipalladium(0) (0.02 g, 0.02 mmol) and 1,1'-bis(diphenylphosphino)ferrocene (0.03 g, 0.05 mmol) in DMF (7 ml, 0.1M) was degassed ($N_2$ purge), then heated at 120° C. for 48 h. The mixture was cooled and filtered through diatomaceous earth, then concentrated in vacuo and the residue was purified by flash silica chromatography DCM:MeOH (97:3) to give the title compound as a yellow oil (80 mg, 26%). NMR 1.22 (t, 3H), 2.52 (s, 3H), 3.15 (q, 2H), 3.27 (s, 3H), 3.42 (t, 2H), 4.41 (q, 2H), 5.08 (t, 1H), 7.75 (d, 1H), 7.83 (d, 1H), 7.90 (s, 1H), 8.18 (s, 1H), 8.68 (s, 1H); m/z 442.

Example 84

2-[4-(2,2-Dimethylaziridin-1-ylsulphonyl)anilino]-4-(1,2-dimethylimidazol-5-yl)pyrimidine To a solution of 2-{4-[N-(1-(4-toluenesulphonyloxy)-2-methylprop-2-yl)sulphamoyl]anilino}-4-(1,2-dimethylimidazol-5-yl)pyrimidine (Method 81; 2.14 g, 3.75 mmol) in acetone (73 ml) was added powdered anhydrous potassium carbonate (0.57 g, 4.13 mmol). The mixture was heated at reflux for 4 hours. The reaction mixture was allowed to cool filtered and the solid washed with acetone. The filtrate was evaporated to give the title compound (1.36 g, 91%) as a white solid. NMR 1.42 (s, 6H), 2.37 (s, 3H), 2.43 (s, 2H), 3.95 (s, 3H), 7.20 (d, 1H), 7.63 (s, 1H), 7.77 (d, 2H), 7.95 (d, 2H), 8.43 (d, 1H), 10.0 (s, 1H), m/z 399.

Example 85

2-[4-(Benzylsulphonyl)anilino]-4-(1-isopropyl-2-methylimidazol-5-yl)pyrimidine 100 vol. Hydrogen peroxide (0.3 ml) was added to a solution of 2-[4-(benzylthio)anilino]-4-(1-isopropyl-2-methylimidazol-5-yl)pyrimidine (Method 50; 160 mg, 0.39 mmol) in glacial acetic acid (2 ml) and the mixture heated at 60-70° C. for one hour. Further hydrogen peroxide (0.3 ml) was added and heating continued for a further 30 minutes. The mixture was diluted and cooled by adding crushed ice and then the solvent was removed by evaporation. The residue was partitioned between DCM (60 ml), saturated aqueous sodium hydrogen carbonate solution (15 ml) and water (10 ml). The organic layer was separated and the aqueous layer re-extracted with DCM (25 ml). The organic extracts were combined, washed with water (20 ml) and brine (15 ml), dried and the volatiles removed by evaporation. The residue was purified by chromatography on silica eluting with DCM/MeOH (98:2). The purified free base product (55 mg) was dissolved in MeOH (3 ml), and 1M HCl in ether (140 µl) added. The volatiles were evaporated and the triturated with ether to give the title compound (53 mg). NMR: 1.52 (d, 6H), 2.80 (s, 3H), 4.61 (s, 2H), 5.58 (m, 1H), 7.19 (m, 2H), 7.31 (m, 4H), 7.60 (d, 2H), 7.90 (d, 2H), 8.21 (s, 1H), 8.74 (d, 1H), 10.30 (s, 1H), 15.00 (br s, 1H); m/z 448.

Example 86

4-(1-Isopropyl-2-methylimidazol-5-yl)-2-[4-(3-morpholinopropylsulphonyl)anilino]pyrimidine A solution of water (0.5 ml) and oxone (400 mg) was added to a solution of 4-(1-isopropyl-2-methylimidazol-5-yl)-2-[4-(3-morpholinopropylthio)anilino]pyrimidine (Method 85; 260 mg, 0.58 mmol) in MeOH (2.5 ml) and acetone (0.5 ml). The mixture was stirred for 4 hours, a solution of sodium metabisulphite (250 mg) in water (1 ml) was added and the mixture stirred for a further 20 minutes. The volatiles were removed by evaporation. Water (10 ml) was added to the residue and saturated aqueous sodium hydrogen carbonate solution added to basify the solution. The aqueous solution was extracted with EtOAc (2×25 ml), the extracts combined, washed with brine (10 ml), dried and evaporated. The residue was purified by chromatography on silica eluting with DCM/MeOH (98:2 increasing in polarity to 92:8). The purified product was dissolved in methanol (4 ml), 1M ethereal hydrogen chloride (270 µl) added and the volatiles removed by evaporation. The residue was triturated with ether to give the title compound (120 mg, 43%). NMR: 1.52 (d, 6H), 1.98 (br t, 2H), 2.62 (s, 3H), 2.88-3.00 (br m, 6H), 3.33 (t, 2H), 3.77 (br s, 4H), 5.53 (sept, 1H), 7.20 (d, 1H), 7.69 (s, 1H), 7.81 (d, 2H), 7.98 (d, 2H), 8.58 (d, 1H), 9.77 (s, 1H); m/z 485.

Example 87

5-Bromo-4-(1-isopropyl-2-methylimidazol-5-yl)-2-(4-mesylanilino)pyrimidine

Bromine (50 µl, 0.94 mmol) was added to a solution of 4-(1-isopropyl-2-methylimidazol-5-yl)-2-(4-mesylanilino)pyrimidine (Example 69; 350 mg, 0.94 mmol) in glacial acetic acid (3.5 ml). The mixture was heated at 60° C. for 140 minutes and the volatiles were then removed by evaporation. The residue was azeotroped with water to give a gum, which was then triturated with EtOAc to give a solid (470 mg). This crude product was purified by chromatography on silica gel eluting with DCM/MeOH (98:2 increasing in polarity to 95:5). The purified product was triturated with EtOAc to give the title compound (125 mg, 30%) as a solid. NMR: 1.39 (d, 6H), 2.48 (s, 3H), 3.12 (s, 3H), 4.68 (sept, 1H), 7.20 (s, 1H), 7.81 (d, 2H), 7.92 (d, 2H), 8.79 (s, 1H), 10.28 (br s, 1H); m/z 450.

Example 88

4-(1-Isopropyl-2-methylimidazol-5-yl)-2-{4-[N-(2-carboxymethyl)sulphamoyl]anilino}pyrimidine 4-(1-Isopropyl-2-methylimidazol-5-yl)-2-{4-[N-(2-methyloxycarbonylmethyl) sulphamoyl]anilino}pyrimidine (Example 41; 90 mg, 0.203 mmol) was added to a stirred solution of lithium hydroxide monohydrate (9.4 mg, 0.23 mmol) in water (5 ml) and MeOH (5 ml). The mixture was stirred at ambient temperature for 18 hours then the volatiles were removed by evaporation. The crude solid residue was dissolved in MeOH (10 ml) and 1M ethereal hydrogen chloride (508 μl, 0.508 mmol) was added and the volatiles removed by evaporation to give the title compound hydrochloride (1:1 mixture with lithium chloride) (104 mg, 100%) as a yellow solid. NMR: 1.51 (d, 6H), 2.82 (s, 3H), 3.51 (s, 2H), 5.64 (m, 1H), 7.27 (d, 1H), 7.69 (d, 2H), 7.90 (d, 2H), 8.23 (s, 1H), 8.67 (s, 1H), 10.29 (s, 1H); m/z 431.

An Example of Process e)—an Alternative Synthesis of Example 69

4-(1-Isopropyl-2-methylimidazol-5-yl)-2-[4-(methylsulphonyl)anilino]pyrimidine Titanium isopropoxide (188 μl, 0.62 mmol) was added to a mixture of 4-(1-isopropyl-2-methylimidazol-5-yl)-2-[4-(methylthio)anilino]pyrimidine (Method 86; 700 mg, 2.06 mmol) in butyl acetate (4.9 ml) and the mixture was heated to 50° C. Cumene hydroperoxide (800 μl, 4.32 mmol) was added over 40 minutes and the mixture was allowed to cool to 20° C. The resulting precipitate was collected by filtration, washed with butyl acetate and dried at 50° C. under vacuum to give the title compound (331 mg, 42%).

Preparation of Starting Materials

The starting materials for the examples above are either commercially available or are readily prepared by standard methods from known materials. For example, the following reactions are an illustration, but not a limitation, of some of the starting materials used in the above reactions.

Methods 1-21

The following compounds were synthesised by the procedure as described in JOC 1987, 2714-2716.

| Meth | Compound | NMR | m/z | SM |
|---|---|---|---|---|
| 1 | 4-(Isopropylamino)-5-methylisoxazole | (CDCl$_3$) 1.12(d, 6H), 2.30(s, 3H), 3.21(1H, sept), 8.01(s, 1H) | 141 | 4-amino-5-methylisoxazole |
| 2 | 5-Methyl-4-(N-isopropylacetamido)isoxazole | (CDCl$_3$) 1.02(brs, 6H), 1.80(s, 3H), 2.38(s, 3H), 4.99(1H, sept), 8.09(s, 1H) | 183 | Meth 1 |
| 3 | 5-Acetyl-1-isopropyl-2-methylimidazole | 1.40(d, 6H), 2.38(s, 3H), 2.42(s, 3H), 5.08(brm, 1H), 7.81(s, 1H) | 167 | Meth 2 |
| 4 | 5-Methyl-4-(N-acetamido)isoxazole | 2.00(s, 3H), 2.34(s, 3H), 8.64(s, 1H), 9.60(brs, 1H) | 141 | 4-amino-5-methylisoxazole hydrochloride |
| 5 | 5-Methyl-4-(ethylamino)isoxazole hydrochloride | 1.21(t, 3H), 2.58(s, 3H), 3.22(q, 2H), 8.76(s, 1H) | 127 | Meth 4 |
| 6 | 5-Methyl-4-(N-ethylacetamido)isoxazole | 0.96(t, 3H), 1.77(s, 3H), 2.36(s, 3H), 3.52(q, 2H), 8.70(s, 1H) | 169 | Meth 5 |
| 7 | 5-Acetyl-1-ethyl-2-methylimidazole | 1.30(t, 3H), 2.40(m, 6H), 4.30(q, 2H), 7.64(s, 1H) | 153 | Meth 6 |
| 8 | 5-Methyl-4-(N-ethylformido)isoxazole | Used crude | | Meth 5 |
| 9 | 5-Acetyl-1-ethylimidazole | 1.23(t, 3H), 2.48(s, 3H), 4.27(q, 2H), 7.86(s, 1H), 7.92(s, 1H) | | Meth 8 |
| 10 | 5-Methyl-4-(N-isopropylformido)isoxazole | Used crude | | Meth 1 |
| 11 | 5-Acetyl-1-isopropylimidazole | 1.38(d, 6H), 2.48(s, 3H), 5.13(q, 2H), 7.86(s, 1H), 8.10(s, 1H) | 153 | Meth 10 |
| 12 | 5-Methyl-4-(N-propionylamido)isoxazole | 1.05(t, 3H), 2.28(q, 2H), 2.35(s, 3H), 8.65(s, 1H), 9.50(s, 1H) | 153 (M − H)$^-$ | 4-amino-5-methylisoxazole hydrochloride |
| 13 | 5-Methyl-4-(propylamino)isoxazole | 0.90(t, 3H), 1.62(m, 2H), 2.53(s, 3H), 3.10(t, 2H), 8.68(s, 1H) | 141 | Meth 12 |
| 14 | 5-Methyl-4-(N-propylformido)isoxazole | 0.82(m, 3H), 1.42(m, 2H), 2.28 & 2.38(s, 3H), 3.50(m, 2H), 8.08 & 8.23(2s, 1H), 8.62 & 8.72(s, 1H) | 167 (M − H)$^-$ | Meth 13 |

| Meth | Compound | NMR | m/z | SM |
|---|---|---|---|---|
| 15 | 5-Acetyl-1-propylimidazole | 0.76(t, 3H), 1.63(m, 2H), 2.40(s, 3H), 4.28(t, 2H), 7.90(s, 1H), 7.95(s, 1H) | 153 | Meth 14 |
| 16 | 5-Methyl-4-(N-propylacetamido)isoxazole | 0.91(t, 3H), 1.50(m, 2H), 1.88(s, 3H), 2.40(s, 3H), 3.52(t, 2H), 8.15(s, 1H) | 183 | 4-amino-5-methylisoxazole hydrochloride |
| 17 | 5-Acetyl-2-methyl-1-propylimidazole | 0.83(t, 3H), 1.60(m, 2H), 2.38(s, 6H), 4.19(dd, 2H), 7.83(s, 1H) | 167 | Meth 16 |
| 18 | 5-Methyl-4-(N-(2-methylpropionyl)amido)isoxazole | 1.07(d, 6H), 1.35(s, 3H), 1.57(m, 1H), 8.65(s, 1H), 9.47(s, 1H) | 169 | 4-amino-5-methylisoxazole hydrochloride |
| 19 | 5-Methyl-4-(isobutylamino)isoxazole | 0.96(d, 6H), 1.95(m, 1H), 2.52(s, 3H), 2.99(d, 2H), 8.68(s, 1H) | 155 | Meth 18 |
| 20 | 5-Methyl-4-[N-(isobutyl)acetamido]isoxazole | 0.81(d, 6H), 1.60(m, 1H), 1.77 & 2.12(s, 3H), 2.24 & 2.36(s, 3H), 3.32(m, 2H), 8.55 & 8.69(s, 1H) | 197 | Meth 19 |
| 21 | 5-Acetyl-1-(isobutyl)imidazole | 0.78(d, 6H), 1.90(m, 1H), 2.32(s, 3H), 2.36(s, 3H), 4.03(d, 2H), 7.83(s, 1H) | 181 | Meth 20 |

Method 22

5-(3-Dimethylaminoprop-2-en-1-oyl)-1,2-dimethylimidazole

2-Methyl-4-acetylimidazole (Tetrahedron letters 1985, 26 (29), 3423-3426; 129 g, 1.04 mol) was dissolved in a mixture of DMF (900 ml) and DMF.DMA (1.51) and the mixture heated under reflux, under an atmosphere of nitrogen, for 18 hours. The reaction mixture was allowed to cool to ambient temperature the product crystallised. The solid product was collected by filtration, washed with DMF.DMA and then ether and dried under vacuum at 40° C. to give the title compound (115 g, 57%) as a pale brown crystalline solid. NMR: 2.13 (s, 3H), 2.95 (s, 6H), 3.78 (s, 3H), 5.56 (d, 1H), 7.50 (d, 1H), 7.53 (s, 1H); m/z 194.

Methods 23-29

The following compounds were synthesised by the procedure of Method 22.

| Meth | Compound | NMR | m/z | SM |
|---|---|---|---|---|
| 23[1] | 5-(3-Dimethylaminoprop-2-en-1-oyl)-1-ethyl-2-methylimidazole | 1.17(t, 3H), 2.16(s, 3H), 2.95(s, 6H), 4.27(q, 2H), 5.57(d, 1H), 7.50(d, 1H), 7.53(s, 1H) | 208 | Meth 7 |
| 24[2] | 5-(3-Dimethylaminoprop-2-en-1-oyl)-1-isopropyl-2-methylimidazole | 1.43(d, 6H), 2.40(s, 3H), 2.95(brs, 6H), 3.31(s, 3H), 5.22(sept, 1H), 5.54(d, 1H), 7.48(s, 1H), 7.52(d, 1H) | 222 | Meth 3 |
| 25 | 5-(3-Dimethylaminoprop-2-en-1-oyl)-1-ethylimidazole | 1.23(t, 3H), 2.95(m, 6H), 4.31(q, 2H), 5.60(d, 1H), 7.55(d, 1H), 7.62(s, 1H), 7.76(s, 1H) | 194 | Meth 9 |
| 26 | 5-(3-Dimethylaminoprop-2-en-1-oyl)-1-isopropylimidazole | 1.43(d, 6H), 2.95(m, 6H), 5.32(m, 1H), 5.58(d, 1H), 7.60(m, 2H), 7.90(s, 1H) | ND | Meth 11 |
| 27 | 5-(3-Dimethylaminoprop-2-en-1-oyl)-1-propylimidazole | 0.75(t, 3H), 1.65(m, 2H), 2.95(br s, 6H), 4.25(t, 2H), 5.62(d, 1H), 7.55(d, 1H), 7.64(s, 1H), 7.66(s, 1H) | 208 | Meth 15 |
| 28 | 5-(3-Dimethylaminoprop-2-en-1-oyl)-1-propyl-2-methylimidazole | 0.80(t, 3H), 1.58(m, 2H), 2.32(s, 3H), 2.95(br s, 6H), 4.22(dd, 2H), 5.58(d, 1H), 7.50(d, 1H), 7.54(s, 1H) | 222 | Meth 17 |
| 29 | 5-(3-Dimethylaminoprop-2-en-1-oyl)-1-(isobutyl)-2-methylimidazole | 400 MHz: 0.78(d, 6H), 1.92(m, 1H), 2.31(s, 3H), 2.95(br s, 6H), 4.12(d, 2H) 5.57(d, 1H), 7.52(d, 1H), 7.57(s, 1H) | 236 | Meth 21 |

[1] Only DMF.DMA used as solvent
[2] Purified by flash chromatography on silica gel eluting with DCM/MeOH(98:2 increasing in polarity to 92.5:7.5)

Method 30

2-Anilino-4-(1-ethyl-2-methylimidazol-5-yl)pyrimidine 5-(3-Dimethylaminoprop-2-en-1-oyl)-1-ethyl-2-methylimidazole (Method 23; 2.10 g, 10.1 mmol), phenylguanidine hydrogen carbonate (2.2 g, 11.1 mmol) and sodium methoxide (1.2 g, 22.2 mmol) were suspended in anhydrous DMA (15 ml) and the mixture heated at 110° C. for 18 hours. The reaction mixture was allowed to cool to ambient temperature and poured into water (50 ml). The solution was extracted EtOAc (2×50 ml). The combined extracts were washed with water (2×50 ml) and then brine (2×50 ml), dried and the volatiles removed by evaporation. The residue was triturated with ether, collected by filtration and air dried to give the title compound (1.48 g, 53%) as a reddish brown solid. NMR 1.17 (t, 3H), 2.38 (s, 3H), 4.52 (q, 2H), 6.93 (t, 1H), 7.08 (d, 1H), 7.27 (t, 2H), 7.60 (s, 1H), 7.62 (d, 2H), 8.35 (d, 1H), 9.35 (s, 1H); m/z 280.

Methods 31-38

The following compounds were synthesised by the procedure of Method 30.

Method 39

2-Amino-4-(1-isopropyl-2-methylimidazol-5-yl)pyrimidine 5-(3-Dimethylaminoprop-2-en-1-oyl)-1-isopropyl-2-methylimidazole (Method 24; 4.9 g, 22.2 mmol) and guanidine hydrochloride (5.3 g, 55.6 mmol) were suspended in 1-butanol (70 ml). NaOMe (4.8 g, 88 mmol) was added in one portion and the mixture heated under reflux, under an atmosphere of nitrogen, for 3 hours. The volatiles were removed by evaporation. Water (50 ml) was added and extracted EtOAc (3×50 ml). The organic layers were combined and dried evaporated in vacuo. The residue triturated with isohexane to give the title compound as a brown solid (1.9 g, 40%). NMR: 1.46 (d, 6H), 2.43 (s, 3H), 5.45 (m, 1H), 6.50 (brs, 1H), 6.74 (d, 1H), 7.28 (s, 1H), 8.12 (d, 1H); m/z 218

Method 40

The following compounds were synthesised by the procedure of Method 39.

| Meth | Compound | NMR | m/z | SM |
|---|---|---|---|---|
| 31[1] | 2-Anilino-4-(1-isopropyl-2-methylimidazol-5-yl)pyrimidine | 1.44(d, 6H), 2.51(s, 3H), 5.72(septuplet, 1H), 6.99(t, 1H), 7.04(d, 1H), 7.30(t, 2H), 7.42(s, 1H), 7.67(d, 2H), 8.39(d, 1H), 9.42(s, 1H) | 294 | Meth 24 |
| 32 | 2-Anilino-4-(1-ethylimidazol-5-yl)pyrimidine | 1.21(t, 3H), 4.55(q, 2H), 6.96(t, 1H), 7.16(d, 1H), 7.29(t, 2H), 7.62(d, 2H), 7.70(s, 1H), 7.86(s, 1H), 8.38(d, 1H), 9.40(s, 1H) | 266 | Meth 25 |
| 33 | 2-Anilino-4-(1-isopropylimidazol-5-yl)pyrimidine | 1.21(d, 6H), 5.65(m, 1H), 6.96(t, 1H), 7.12(d, 1H), 7.29(t, 2H), 7.63(m, 3H), 8.04(s, 1H), 8.38(d, 1H), 9.40(s, 1H) | 280 | Meth 26 |
| 34[2] | 2-Anilino-4-(1,2-dimethylimidazol-5-yl)pyrimidine | 2.37(s, 3H), 3.93(s, 3H), 6.95(t, 1H), 7.08(d, 1H), 7.28(t, 2H), 7.59(s, 1H), 7.69(d, 2H), 8.35(d, 1H), 9.43(s, 1H) | 266 | Meth 22 |
| 35 | 2-(2-Fluoroanilino)-4-(1,2-dimethylimidazol-5-yl)pyrimidine | 2.33(s, 3H), 3.75(s, 3H), 7.07(d, 1H), 7.17(m, 3H), 7.58(s, 1H), 7.65(t, 1H), 8.30(d, 1H), 9.02(s, 1H) | 284 | Meth 22 Meth 70 |
| 36 | 2-Anilino-4-(1-propylimidazol-5-yl)pyrimidine | 0.68(t, 3H), 1.55(m, 2H), 4.48(t, 2H), 6.97(t, 1H), 7.14(d, 1H), 7.30(t, 2H), 7.63(d, 2H), 7.73(s, 1H), 7.88(s, 1H), 8.38(d, 1H), 9.40(s, 1H) | 280 | Meth 27 |
| 37 | 2-Anilino-4-(2-methyl-1-propylimidazol-5-yl)pyrimidine | 0.62(t, 3H), 1.50(m, 2H), 2.38(s, 3H), 4.46(t, 2H), 6.98(t, 1H), 7.06(d, 1H), 7.28(t, 2H), 7.55–7.65(m, 3H), 8.35(d, 1H), 9.36(s, 1H) | 294 | Meth 28 |
| 38 | 2-Anilino-4-[1-(2-methylpropyl)-2-methylimidazol-5-yl]pyrimidine | 400 MHz: 0.63(d, 6H), 1.70(m, 1H), 2.37(s, 3H), 4.36(d, 2H), 6.95(t, 1H), 7.08(d, 1H), 7.29(t, 2H), 7.60(s, 1H), 7.64(d, 2H), 8.35(d, 1H), 9.40(s, 1H). | 308 | Meth 29 |

[1] Solid crystallised from EtOAc
[2] Recrystallized from MeOH

| Meth | Compound | NMR | m/z | SM |
|---|---|---|---|---|
| 40 | 2-Amino-4-(1,2-dimethylimidazol-5-yl)pyrimidine | 2.16(s, 3H), 3.93(s, 3H), 6.52(s, 2H), 6.80(d, 1H), 7.47(s, 1H), 8.17(d, 1H) | 190 | Meth 22 |

Method 41

N-(1,1-Dimethyl-2-(4-iodosulphonyloxy)-ethyl)-4-iodosulphonamide

2-Amino-2-methyl-1-propanol (1.34 g, 15 mmol) was dissolved in dry pyridine and cooled to 0° C. under inert gas. Pipsyl chloride (9.52 g, 31.5 mmol) was added in portions as a solid keeping temperature <2° C. The stirred a further 10 minutes at 0° C. and then at room temperature for 18 hr. The reaction mixture was poured into vigorously stirred ice water and the pH adjusted to 1.0 using conc. HCl. The precipitated solid was filtered washed with water and dried to give the title compound (7.03 g, 75%) as a brown solid; NMR (CDCl$_3$) 1.29 (s, 6H), 3.93 (s, 2H), 4.76 (s, 1H), 7.55 (m, 4H), 7.82 (d, 2H), 7.73 (d, 2H).

Method 42

2,2-Dimethylaziridin-1-yl-4-iodosulphonamide

To a stirred solution of N-(1,1-dimethyl-2-(4-iodosulphonyloxy)-ethyl)-4-iodosulphonamide (Method 41; 7.0 g, 11.27 mmol) in acetone (112 ml) was added powdered anhydrous potassium carbonate (1.71 g, 12.4 mmol). The mixture was heated at reflux for 20 hours and left standing at room temperature for 2 days. The reaction mixture was filtered and the solid washed with acetone. The filtrate was evaporated in vacuo. The crude product was purified by flash silica chromatography DCM:isohexane (3:1) to give the title compound (3.36 g, 88%) as a white solid. NMR (CDCl$_3$) 1.53 (s, 6H), 2.43 (s, 2H), 7.63 (d, 2H), 7.85 (d, 2H); m/z 337.

Method 43

N-(1,1-Dimethyl-2-methoxyethyl)-4-iodosulphonamide

To a stirred solution of 2,2-dimethylaziridin-1-yl-4-iodosulphonamide (Method 42; 3.35 g, 9.94 mmol) in dry THF (100 ml), under inert gas atmosphere was added rapidly NaOMe (2.68 g, 49.7 mmol. The suspension was heated at reflux under inert gas for 6 hours. The reaction mixture was allowed to cool and then poured onto a stirred mixture of distilled water and acetic acid (3.2 ml, 22.4 mmol). Ether (100 ml) was added, washed with water (100 ml), dried and the solvent evaporated in vacuo. The crude product was triturated with ether/isohexane, filtered, washed with i-hexane and dried to give the title compound (2.44 g, 67%) as a white solid. NMR 1.03 (s, 6H), 3.07 (s, 3H), 3.1 (s, 2H), 7.55 (m, 3H), 7.93 (d, 2H); m/z 370.

Method 44

N-(2-Ethoxyethyl)-4-iodobenzenesulphonamide

2-Ethoxyethylamine (2.14 g, 24 mmol) and diisopropylethylamine (4.2 ml, 24 mmol) were dissolved in DCM (50 ml) and cooled to 0° C. To this was added pipsyl chloride (6.05 g, 20 mmol) in portions and the reaction stirred for 18 hours. Volatiles were evaporated in vacuo. The residue was dissolved in EtOAc (50 ml), washed with 0.33M citric acid (2×50 ml), brine (50 ml), dried and evaporated in vacuo to yield an oil which solidified on standing to give the title compound as a pale yellow solid (6.97 g, 98%). NMR: 1.01 (t, 3H), 2.89 (q, 2H), 3.30 (m, 4H), 7.53 (d, 2H), 7.75 (t, 1H), 7.97 (d, 2H); m/z 354 (M–H)$^-$.

Method 45

N-(2-Hydroxyethyl)-4-iodobenzenesulphonamide

The title compound was prepared by the procedure of Method 44 using the appropriate starting materials. NMR: 2.79 (t, 2H), 3.35 (m, 2H), 4.62 (t, 1H), 7.55 (d, 2H), 7.62 (s, 1H), 7.98 (d, 2H); m/z 326 (M–H)$^-$.

Method 46

N-(2-methansulphonyloxyethyl)-4-iodobenzenesulphonamide

Diisopropylethylamine (585 µl, 3.36 mmol) followed by methane sulphonyl chloride (260 µl, 3.36 mmol) was added to a stirred solution of N-(2-hydroxyethyl)-4-iodobenzenesulphonamide (Method 45; 1 g, 3.06 mmol) in EtOAc (25 ml) at 5° C., under nitrogen. The reaction was allowed to warm to ambient temperature and stirred for 24 hours. The reaction mixture was washed with 1M hydrochloric acid (3×25 ml), saturated aqueous sodium hydrogen carbonate solution (3×25 ml), brine (2×25 ml), an then dried. The volatiles were removed by evaporation and the residue purified by chromatography on silica, eluting with DCM/MeOH (100:0 increasing in polarity to 99:1) to give the title compound (562 mg, 45%) as a white solid. NMR: 3.08 (m, 2H), 3.12 (s, 3H), 4.08 (t, 2H), 7.55 (d, 2H), 7.98 (d, 2H), 8.03 (t, 1H); m/z 405.

Method 47

N-(2-Cyclopropylmethoxyethyl)-4-iodobenzenesulphonamide

Sodium hydride (136 mg of a 60% suspension in mineral oil, 3.39 mmol) was slowly added to a stirred solution of cyclopropylmethanol (275 µl, 3.39 mmol) in DMF (8 ml), at 0° C. under nitrogen. The mixture was stirred for 20 minutes, then a solution of N-(2-methansulphonyloxyethyl)-4-iodobenzenesulphonamide (Method 46; 550 mg, 1.36 mmol) in DMF (6 ml) was slowly added and the reaction allowed to warm to ambient temperature and stirred for 18 hours. The volatiles were removed by evaporation and water (30 ml) added to the residue. The aqueous solution was extracted with EtOAc (3×20 ml), the extracts were combined washed with water (3×40 ml), brine (2×30 ml), dried and volatiles removed by evaporation. The residue was purified by chromatography on silica eluting with DCM/MeOH (100:0 increasing in polarity to 99:1) to give the title compound (328 mg, 74%) as a colourless oil, which solidified upon standing. NMR: 0.09 (m, 2H), 0.40 (m, 2H), 0.89 (m, 1H), 2.90 (m, 2H), 3.11 (d, 2H), 3.33 (t, 2H), 7.55 (d, 2H), 7.77 (t, 1H), 7.96 (d, 2H); m/z 380 (M–H)$^-$.

Method 48

1-(Tetrahyrofur-2-ylmethylsulphonyl)-4-bromobenzene

4-Bromothiophenol (1.9 g, 10 mmol) and potassium carbonate (1.5 g, 11 mmol) were stirred in acetone (40 ml). Tetrahydrofurfurylbromide (2 g, 12 mmol) was added dropwise, and the mixture was then heated at 45° C. for 2 hours. The mixture was allowed to cool, the insolubles removed by filtration and the filter pad washed with acetone. The volatiles were removed from the filtrate by evaporation to give crude 1-(2-tetrahyrofurylmethylthio)-4-bromobenzene (3.1 g) an oil (m/z 273). This crude product was dissolved in methanol (60 ml) and water (10 ml). Oxone (8 g) added in portions and the mixture stirred for 2.5 hours. Water (20 ml) was added and the methanol was removed by evaporation. Further water (20 ml) was added to the aqueous residue, which was then extracted with DCM (2×50 ml). The extracts were combined, washed with brine (15 ml), dried and the solvent evaporated. The residue was purified by chromatography on silica eluting with DCM/isohexane/EtOAc (10:8:2) to give the title compound (1.7 g, 56%) as a solid. NMR (CDCl$_3$): 1.56 (m, 1H), 1.88 (m, 2H), 2.13 (m, 1H), 3.20 (dd, 1H), 3.39 (dd, 1H), 3.72 (m, 2H), 4.26 (m, 1H), 7.68 (d, 2H), 7.79 (d, 2H); m/z 305.

Method 49

1-(3-Ethoxypropylsulphonyl)-4-bromobenzene

1-Bromo-3-ethoxypropane (2.2 g, 13.3 mmol) was treated as described in the Method 48 to give the title compound (2.9 g, 71%). NMR (CDCl$_3$): 1.12 (t, 3H), 1.98 (m, 2H), 3.20 (m, 2H), 3.42 (m, 4H), 7.70 (d, 2H), 7.78 (d, 2H); m/z 307.

Method 50

2-[4-(Benzylthio)anilino]-4-(1-isopropl-2-methylinidazol-5-yl)pyrimidine

The title compound was prepared by the procedure of Example 67 using the appropriate starting materials. NMR: 1.48 (d, 6H), 2.77 (s, 3H), 4.12 (s, 2H), 5.58 (m, 1H), 7.14 (m, 1H), 7.20 (m, 1H), 7.28 (m, 6H), 7.59 (d, 2H), 8.18 (s, 1H), 8.61 (d, 1H), 9.79 (s, 1H); m/z 416.

Method 51

1-(1-Methylcyclopropane)carboxamide

Oxalyl chloride (8.24 ml, 0.095 mol) and then DMF (few drops) were added to a solution of 1-(1-methylcyclopropane)carboxylic acid (9.42 g, 0.094 mol) in DCM (150 ml) cooled at 5° C. and the mixture stirred at 5° C. for 30 minutes and then for 3 hours at ambient temperature. The solvent and excess oxalyl chloride were removed by evaporation, the residue dissolved in DCM and added to a solution of ammonia (excess) in MeOH cooled at 5° C. The mixture was allowed to warm to ambient temperature and the volatiles removed by evaporation to give the title compound. NMR: 0.29 (q, 2H), 0.71 (q, 2H), 1.02 (s, 3H), 6.62 (s, 1H), 6.85 (s, 1H).

Method 52

1-Amino-1-methylcyclopropane

Bromine (2.87 ml, 0.056 mol) was added to a solution of sodium hydroxide (13.5 g, 0.338 mol) in water (100 ml) at 0-5° C. A slurry of 1-(1-methylcyclopropane)carboxamide (Method 51; 5.70 g 0.056 mol) in water (50 ml) was then added and reaction mixture stirred at 5° C. for 2 hours, then left to stand at ambient temperature for 24 hours. The mixture was then heated at 80° C. for 2.5 hours, allowed to cool and mixture distilled to give the title compound (bp 75-80° C.). NMR: 0.2 (q, 2H), 0.14 (q, 2H), 0.96 (s, 3H), 1.42 (s, 2H).

Method 53

1,3-Dimethoxy-2-methanesulphonyloxypropane

To a solution of 1,3-dimethoxy-2-hydroxypropane (3.84 g, 0.032 mol) in DCM (70 ml) cooled at 5° C. was added triethylamine (5 ml, 0.036 mol) followed by slow addition of methanesulphonyl chloride (2.72 ml, 0.035 mol). The mixture was then stirred at ambient temperature for 24 hours. The mixture was then absorbed onto silica gel and purified by flash silica chromatography DCM:isohexane (3:1) to give the title compound (3.74 g, 59%). NMR 3.15 (s, 3H), 3.28 (s, 6H), 3.52 (d, 4H), 4.78 (q, 1H).

Methods 54-55

The following compounds were prepared by the procedure of Method 53 using the appropriate starting materials.

| Meth | Compound | NMR |
|---|---|---|
| 54 | 1-Ethoxy-2-methanesulphonyloxypropane | 1.10(t, 3H), 1.28(d, 3H), 3.14(s, 3H), 3.42–3.48(m, 2H), 3.65(m, 2H), 4.78(q, 1H) |
| 55 | 1-Propoxy-2-methanesulphonyloxypropane | 0.86(t, 3H), 1.28(d, 3H), 1.51(q, 2H), 3.33–3.40(m, 2H), 3.44(d, 2H), 3.69(d, 3H), 4.78(q, 1H) |

Method 56

1,3-Dimethoxy-2-azidoitropane 1,3-Dimethoxy-2-methanesulphonyloxypropane (Method 53; 3.74 g, 19 mmol) and sodium azide (2.03 g, 31 mmol) in DMA (55 ml) was heated at 100° C. for 8 hours then left to stand at ambient temperature for 24 hours. The mixture was diluted with water, extracted with EtOAc, the extracts combined and washed with water, dried and the volatiles removed by evaporation to give the title compound (2.0 g, 74%) as a clear oil.

Methods 57-58

The following compounds were prepared by the procedure of Method 56 using the appropriate starting materials.

| Meth | Compound | SM |
|---|---|---|
| 57 | 1-Ethoxy-2-azidopropane | Method 54 |
| 58 | 1-propoxy-2-azidopropane | Method 55 |

Method 59

1,3-Dimethoxy-2-aminopropane

10% Palladium on charcoal (500 mg) was added to a solution of 1,3-dimethoxy-2-azidopropane (Method 56; 2 g, 0.014 mol) in ethanol (40 ml) and the mixture stirred under an atmosphere of hydrogen at ambient temperature for 6 hours. The catalyst was removed by filtration through diatomaceous earth and the filter pad washed with ethanol to give a solution of the title compound in ethanol (20 ml).

Methods 60-61

The following compounds were prepared by the procedure of Method 59 using the appropriate starting materials.

| Meth | Compound | SM |
|------|----------|-----|
| 60 | 1-Ethoxy-2-aminopropane | Method 57 |
| 61 | 1-propoxy-2-aminopropane | Method 58 |

Method 62

1-[3-(N,N-Dimethylamino)propylthio]-4-bromobenzene 3-(Dimethylamino)propyl chloride hydrochloride (3.48 g, 22 mmol) was added in portions to a suspension of 4-bromothiophenol (3.78 g, 20 mmol) and potassium carbonate (5.52 g, 40 mmol) in DMF (40 ml) and the reaction mixture heated to 60° C. for 15 minutes. The mixture was allowed to cool to ambient temperature and poured into water (100 ml) and extracted with EtOAc (2×100 ml). The extracts were combined, washed with brine (3×100 ml), dried (Chemelut column 1010) and evaporated to give the title compound (5.25 g, 96%) as a pale yellow oil. NMR 1.76 (m, 2H), 2.20 (s, 6H), 2.35 (t, 2H), 2.93 (t, 2H), 7.18 (d, 2H), 7.38 (d, 2H); m/z 276.

Method 63

1-(3,3,3-Trifluoropropylthio)-4-bromobenzene

3-Bromo-1,1,1-trifluoropropane (640 µl, 6 mmol) was added to a mixture of 4-bromothiophenol (945 mg, 5 mmol) and potassium carbonate (760 mg, 5.5 mmol) in DMF (5 ml) and the reaction mixture heated at 40° C. for 1 hour. The mixture was allowed to cool to ambient temperature and poured into water (50 ml) and extracted with EtOAc (2×30 ml). The extracts were combined, washed with brine (3×30 ml), dried (Chemelut column 1010) and evaporated to give the title compound (1.36 g, 95%) as a pale yellow oil. NMR 2.56 (m, 2H), 3.13 (t, 2H), 7.31 (d, 2H), 7.51 (d, 2H); m/z 285 (M$^+$).

Method 64

1-(1-Butylthio)-4-bromobenzene

The title compounds was synthesised in an analogous method to Method 63. NMR 0.85 (t, 3H), 1.38 (m, 2H), 1.51 (m, 2H), 2.96 (t, 2H), 7.23 (d, 2H), 7.46 (d, 2H); m/z 244 (M$^+$).

Method 65

1-[3-(N,N-Dimethylamino)propylsulphonyl]-4-bromobenzene

Oxone (14 g, 23 mmol) was added to a solution of 1-[3-(N,N-dimethylamino)propylthio]-4-bromobenzene (Method 62; 5.24 g, 19.1 mmol) in MeOH (150 ml) and water (30 ml) and the mixture was stirred at ambient temperature for 90 minutes. The reaction mixture was poured onto an Isolute SCX-2 column, washed MeOH (6×40 ml) and the product eluted with 2% methanolic ammonia (10×40 ml). The solvent was evaporated and residue purified by flash chromatography on silica gel eluting with DCM/2% methanolic ammonia (100:0 increasing in polarity to 94:6) to yield the title compound (4.68 g, 80%) as a pale yellow oil. NMR 1.62 (m, 2H), 2.03 (s, 6H), 2.19 (t, 2H), 3.32 (m, 2H), 7.81 (m, 4H); m/z 306.

Method 66

1-(3,3,3-Trifluoropropylsulphonyl)-4-bromobenzene

Oxone (3.7 g, 6 mmol) was added to a solution of 1-(3,3,3-trifluoropropylthio)-4-bromobenzene (Method 63; 1.36, 4.75 mmol) in MeOH (25 ml) and water (5 ml) and the mixture was stirred at ambient temperature for 18 hours. The MeOH evaporated and water (20 ml) added and the mixture extracted with DCM. The extracts were dried (Chemelut column CE1005) and solvent removed by evaporation to give the title compound (1.43 g, 95%) as a white solid. NMR 2.62 (m, 2H), 3.67 (m, 2H), 7.86 (s, 4H); m/z 316 (M$^+$).

Method 67

1-(1-Butylsulphonyl)-4-bromobenzene

The title compound was synthesised from Method 64 in an analogous method to Method 66. NMR: 0.80 (t, 3H), 1.31 (m, 2H), 1.47 (m, 2H), 3.29 (t, 2H), 7.78 (d, 2H), 7.86 (d, 2H); m/z 276 (M$^+$).

Method 68

3-Methoxy-1-propanol methanesulphonate

Methanesulphonyl chloride (1.75 ml, 22 mmol) was added to a solution of 3-methoxy-1-propanol (1.81 g, 20 mmol) and triethylamine (3.35 ml, 24 mmol) in DCM (40 ml) cooled in an ice bath and the mixture stirred at ambient temperature for 18 hours. DCM (25 ml) and water (50 ml) were added and the phases separated and the aqueous layer was extracted with DCM (25 ml). The extracts were combined, washed with water (50 ml) and brine (50 ml), dried (Chemelut column CE1010) and evaporated to give the title compound 3.25 g (97%) as a pale yellow oil. NMR 2.00 (m, 2H), 3.01 (s, 3H), 3.35 (s, 3H), 3.49 (t, 2H), 4.38 (t, 2H).

Method 69

1-(3-Methoxypropylsulphonyl)-4-bromobenzene

Potassium carbonate (2.8 g, 20 mmol) was added to a solution of 3-methoxypropan-1-yl methansulphonate (Method 68; 3.25 g, 19.3 mmol) and 4-bromothiophenol (3.48 g, 18.4 mmol) in DMF (30 ml) and the mixture heated at 40° C. for 4 hours. The mixture was allowed to cool to ambient temperature, poured into water (100 ml) and extracted with EtOAc (2×50 ml). The extracts were combined, washed with saturated aqueous sodium hydrogen carbonate solution (50 ml) and brine (2×50 ml), dried (Chemelut column CE1010) and the volatiles removed by evaporation. The residue was dissolved in MeOH (150 ml) and water (30 ml) and oxone (13.4 g, 21.6 mmol) was added in portions. The mixture was stirred at ambient temperature for 18 hours. The MeOH was evaporated, water (50 ml) added and the solution extracted with DCM (3×50 ml). The extracts were combined, washed with brine (50 ml), dried (Chemelut column CE1010), and evaporated. The residue was purified by flash chromatography on silica gel eluting with iso-hexane: EtOAc (100:0 increasing in polarity to 90:10) to give the title compound (3.32 g, 62%) as a colourless oil. NMR 1.95 (m, 2H), 3.19 (m, 2H), 3.26 (s, 3H), 3.41 (t, 2H), 7.70 (d, 2H), 7.78 (d, 2H).

Method 70

2-Fluorophenylguanidine Bicarbonate

Concentrated hydrochloric acid (6 ml) in water (4.8 ml) was added to a mixture of 2-fluoroaniline (7.94 g, 71.2 mmol) and cyanamide (6.98 g, 166 mmol) and the mixture heated at 115° C. for 2.5 hours. The reaction mixture was allowed to cool to ambient temperature and the solution was adjusted to pH 13 by careful addition of 40% aqueous sodium hydroxide solution. The aqueous solution was extracted with EtOAc and the combined organic extracts were dried ($Na_2SO_4$) and the volatiles removed by evaporation. The crude product was dissolved in water (40 ml) and carbon dioxide gas bubbled through the solution until the pH of the suspension remained constant (approximately pH 9). The precipitated solid was collected by filtration, washed sparingly with water and dried to give the title compound (11.95 g, 78%) as a white solid. NMR: 6.83 (m, 2H), 7.0 (m, 2H); m/z: 154.

Methods 71-72

The following compounds were prepared by the procedure of Example 46 using the appropriate starting materials.

Method 74

Ethynylcarbamoyl

To liquid ammonia (300 ml) was added methyl propiolate (52.4 g, 0.62 mol) over 2 hours keeping the temperature at −70° C. The ammonia was left to evaporate and the reaction mixture evaporated in vacuo to yield the title compound (43 g) which was used without any further purification. Mpt: 54-55° C.

Method 75

3-Oxo-2,3-dihydro-1,2,5-thiadiazole

To a stirred solution of ethynylcarbamoyl (Method 74; 43 g, 0.62 mol) in water (310 ml) cooled in ice bath was added ammonium thiosulphate (92.35 g, 0.62 mol) in one portion. The reaction was allowed to warm to room temperature over 5 hours. To the reaction mixture was added a solution of iodine (79.2 g, 0.31 mol) in MeOH (1l) rapidly over 10 minutes to yield a dark solution. Ammonium thiosuphate was added until a yellow solution was obtained. The solvent was

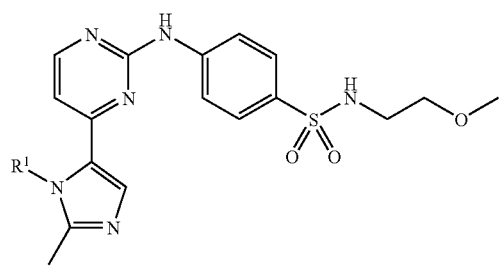

| Meth | R[1] | NMR | M/z | SM |
|---|---|---|---|---|
| 71[1] | Et | 1.25(t, 3H), 2.40(s, 3H), 3.05(q, 2H), 3.20(s, 3H), 3.36(t, 2H), 4.43(q, 2H), 4.92(t, 1H), 6.95(d, 1H), 7.32(brs, 1H), 7.50(s, 1H), 7.72(m, 4H), 8.35(d, 1H) | 417 | Meth 30 |
| 72[1] | i-Pr | 1.48(d, 6H), 2.51(s, 3H), 2.86(m, 2H), 3.16(s, 3H), 3.29(t, 2H), 5.66(septuplet, 1H), 7.14(d, 1H), 7.46(s, 1H), 7.49(t, 1H), 7.69(d, 2H), 7.89(d, 2H), 8.45(d, 1H), 9.88(s, 1H) | 431 | Meth 31 |

Method 73

3-Hydroxyisoxazole

Hydroxylamine hydrochloride (35 g, 0.5 mol) was added to a solution of sodium hydroxide (58 g, 1.45 mol) in water (580 ml). MeOH (600 ml) followed by ethyl propiolate (38 ml, 0.37 mol) in portions was then added and the resulting solution stirred at ambient temperature for 6 days. The mixture was acidified to pH2 with concentrated hydrochloric acid and then saturated with sodium chloride. The solution was extracted with DCM (8×500 ml), the extracts combined, dried and the solvent evaporated. The solid residue was washed with hot iso-hexane (3×300 ml) and the final suspension was allowed to cool and the resulting solid was collected by filtration, dried under vacuum to give the title compound (11.16 g, 35%) as a white solid crystallised. NMR 6.04 (s, 1H), 8.43 (s, 1H), 11.16 (s, 1l). m/z 85 (M+).

evaporated to approximately 400 ml and extracted ether (3×300 ml). The ethereal solution was washed brine (100 ml), passed through phase separation paper and evaporated in vacuo to yield the title compound as a pale orange solid (32.8 g, 52%). Mpt: 70-71° C.

Method 76

3-[2-(t-Butoxycarbonylamino)ethoxy]-1,2,5-thiadiazole

Diisopropyl azodicarboxylate (1.1 ml, 5.5 mmol) was added dropwise to a solution of 2-(t-butoxycarbonylamino) ethanol (850 µl, 5.5 mmol), 3-oxo-2,3-dihydro-1,2,5-thiadiazole (Method 75; 510 mg, 5 mmol) and triphenylphosphine (1.44 g, 5.5 mmol) in THF (20 ml) and the mixture was stirred at ambient temperature for 18 hours. The solvent was evaporated and the residue purified by flash chromatography on silica gel eluting with iso-hexane:EtOAc (100:0 increasing in polarity to 4:1) to give the title compound (1.17 g, 95%) as a white solid. NMR 1.38 (s, 9H), 3.31 (m, 2H), 4.16 (t, 2H), 6.96 (m, 1H), 8.35 (s, 1H); m/z 246.

Method 77

The following compound was synthesised in an analogous method to Method 76 using the appropriate amine and heterocycle as starting materials.

| Meth | Compound | NMR | m/z | SM |
|---|---|---|---|---|
| 57 | 3-[3-(t-Butoxycarbonylamino)propoxy]isoxazole | 1.36 (s, 9H), 1.80 (m, 2H), 3.04 (q, 2H), 4.17 (t, 2H), 6.24 (s, 1H), 6.83 (m, 1H), 8.61 (s, 1H) | 243 | Meth 73 |

Method 78

3-(2-Aminoethoxy)-1,2,5-thiadiazole Hydrochloride

4M Hydrogen chloride in dioxane (10 ml) was added to a solution of 3-[2-(t-butoxycarbonylamino)ethoxy]-1,2,5-thiadiazole (Method 76; 1.17 g, 4.74 mmol) in dioxane (20 ml) and the mixture was stirred at ambient temperature for 2 days. The resulting solid was collected by filtration, washed with ether and dried to give the title compound (803 mg, 93%) as a white solid NMR 3.20 (m, 2H), 4.58 (t, 2H), 8.36 (m, 4H); m/z 146.

Method 79

The following compound was synthesised in an analogous method to Method 78.

| Meth | Compound | NMR | m/z | SM |
|---|---|---|---|---|
| 79 | 3-(3-Aminopropoxy)isoxazole hydrochloride | 2.02 (m, 2H), 2.83 (m, 2H), 4.24 (t, 2H), 6.29 (s, 1H), 8.20 (s, 3H), 8.61 (s, 1H) | 143 | Meth 77 |

Method 80

5-Bromo-4-(1-ethyl-2-methylimidazol-5-yl)-2-{4-[N-(2-methoxyethyl)sulphamoyl]anilino}pyrimidine Bromine (8 μl, 0.14 mmol) was added to a solution of 4-(1-ethyl-2-methylimidazol-5-yl)-2-{4-[N-(2-methoxyethyl)sulphamoyl]anilino}pyrimidine (Method 71; 52 mg, 0.13 mmol) in glacial acetic acid (2 ml) heated at 60° C. The mixture was heated at 60° C. for 4 hours, then the solvent was removed by evaporated. The residue was dissolved in DCM (20 ml), washed with saturated aqueous sodium hydrogen carbonate solution (20 ml), dried (Chemelut column 1005) and purified by flash chromatography eluting with DCM/2% methanolic ammonia (100:0 increasing in polarity to 97:3) to yield the title compound (37 mg, 60%) as a white foam NMR 1.25 (t, 3H), 2.50 (s, 3H), 3.15 (q, 2H), 3.26 (s, 3H), 3.42 (t, 2H), 4.33 (q, 2H), 4.92 (t, 1H), 7.40 (s, 1H), 7.71 (d, 2H), 7.82 (m, 3H), 8.61 (s, 1H); m/z 497.

Method 81

2-{4-[N-(1-(4-Toluenesulphonyloxy)-2-methylprop-2-yl)sulphamoyl]anilino}-4-(1,2-dimethylimidazol-5-yl)pyrimidine 2-{4-[N-(1-Hydroxy-2-methylprop-2-yl)sulphamoyl]anilino}-4-(1,2-dimethylimidazol-5-yl)pyrimidine (Example 59; 2.36 g, 5.66 mmol) was dissolved in dry pyridine (55 ml) and the solution stirred and cooled to 0° C. under inert gas. Solid p-toluenesulphonyl chloride (5.61 g, 29.4 mmol) was added portionwise over 2 minutes. The reaction was stirred at 0° C. for 10 minutes and then at room temperature for 18 hr. The reaction mixture was diluted with water (200 ml) and the precipitated oil allowed to settle out. The supernatant water layer was decanted off and the residual oil was washed with more water and this was decanted off. This process was repeated and then the oil partitioned between EtOAc (100 ml) and water (50 ml). The layers were separated and the organic layer washed with water (50 ml), dried and the solvent evaporated in vacuo to yield the title compound as a gum (1.94 g, 60%) NMR 1.0 (s, 6H), 2.36 (s, 3H), 2.38 (s, 3H), 3.77 (s, 2H), 3.93 (s, 3H), 7.20 (d, 1H), 7.43 (d, 2H), 7.55 (s, 1H), 7.65 (m, 5H), 7.87 (d, 2H), 8.45 (d, 1H), 9.9 (s, 1H); m/z 571.

Method 82

1-(3-Hydroxypropylthio)-4-nitrobenzene

3-Chloropropanol (6.0 g, 63.5 mmol) was added dropwise to a solution of 4-nitrothiophenol (8.2 g, 52.9 mmol) and sodium hydroxide (3.2 g) in water (120 ml) stirred and heated at 80° C. under nitrogen and the mixture heated at 80° C. for 205 minutes. The mixture was allowed to cool and then extracted with EtOAc (2×100 ml). The extracts were combined, washed with water (50 ml) and brine (50 ml), dried and evaporated to give the title compound (11.1 g, 98%). NMR (CDCl$_3$) 1.99 (m, 2H), 3.18 (t, 2H), 3.81 (m, 2H), 7.35 (d, 2H), 8.13 (d, 2H).

Method 83

4-(3-Hydroxypropylthio)aniline

Iron powder (330 mg) and conc. hydrochloric acid (0.3 ml) were added to a solution of 1-(3-hydroxypropylthio)-4-nitrobenzene (Method 82; 1 g, 4.69 mmol) in ethanol (6 ml) and water (3 ml). The mixture was stirred and heated at 90° C. for 3 hours, further iron powder (300 mg) and conc. HCl (0.2 ml) were added and heating continued for a further 2 hours. The volatiles were removed by evaporation and water (20 ml) added to the residue. The mixture was acidified to pH 1 with 2M hydrochloric acid, filtered through diatomaceous earth, and the filtrate washed with EtOAc (2×25 ml). The aqueous layer was basified to pH11 with conc. aqueous sodium hydroxide solution and extracted with EtOAc (2×25 ml). The extracts were combined, washed with brine (15 ml), dried and evaporated under reduced pressure to give the title compound (900 mg, 100%). m/z 184.

Method 84

4-(1-Isopropyl-2-methylimidazol-5-yl)-2-[4-(3-hydroxypropylthio)anilino]pyrimidine 2M Hydrochloric acid (10 ml) and cyanamide (500 mg) were added to a solution of 4-(3-hydroxypropylthio)aniline (Method 83; 900 mg) in ethanol (1 ml). The mixture was stirred under reflux for 19 hours and further 2M hydrochloric acid (0.5 ml) and cyanamide (400 mg) were added and heating continued for a further 6 hours. The volatiles were removed by evaporation, water (5 ml) was added to the residue and the mixture basified with concentrated sodium hydroxide solution to greater than pH11. The aqueous mixture was extracted with EtOAc (2×30 ml) washed with water (5 ml) and brine (10 ml). The organic extracts were combined, evaporated, and azeotroped with methanol to give crude 4-(3-hydroxypropylthio) phenylguanidine (880 mg) as a purple oil (m/z 226). This crude product was treated with 5-(3-dimethylaminoprop-2-en-1-oyl)-1-isopropyl-2-methylimidazole (Method 24; 400 mg, 1.81 mmol) as described in Method 30 to give the title compound (400 mg, 58%). NMR: 1.44 (d, 6H), 1.68 (m, 2H), 2.92 (t, 2H), 3.34 (s, 3H), 3.49 (m, 2H), 4.52 (t, 1H), 5.70 (sept, 1H), 7.05 (d, 1H), 7.30 (d, 2H), 7.42 (s, 1H), 7.64 (d, 2H), 8.39 (d, 1H), 9.51 (s, 1H); m/z 384.

Method 85

4-(1-Isopropyl-2-methylimidazol-5-yl)-2-[4-(3-morpholinopropylthio)anilino]pyrimidine 4-(1-Isopropyl-2-methylimidazol-5-yl)-2-[4-(3-hydroxypropylthio)anilino]pyrimidine (Method 84; 250 mg, 0.65 mmol) was suspended in DCM (8 ml) and acetonitrile (2 ml) and the stirred at room temperature under nitrogen. Triethylamine (100 μl) was added followed by dropwise addition of methane sulphonyl chloride (50 μl). The mixture was stirred for 2.5 hours and then allowed to stand for 18 hours. The volatiles were removed by evaporation, the residue dissolved in acetonitrile (5 ml), and morpholine (120 μl) and potassium carbonate (50 mg) were added. The mixture was stirred and heated at 80° C. for 3.5 hours and then the volatiles were removed by evaporation. The residue was partitioned between EtOAc (50 ml) and water (20 ml). The aqueous layer was basified to pH 9 with sodium bicarbonate solution. The phases separated and the aqueous layer re-extracted with EtOAc. The extracts were combined, washed with water (10 ml) and brine (10 ml), dried and then evaporated to give the title compound (260 mg, 88%) m/z 453.

Method 86

4-(1-Isopropyl-2-methylimidazol-5-yl)-2-[4-(methylthio)anilino]pyrimidine

A mixture of N-[4-(methylthio)phenyl]guanidine[1] (1 g, 5.5 mmol) and 5-(3-dimethylaminoprop-2-en-1-oyl)-1-isopropyl-2-methylimidazole (Method 24; 1.22 g, 5.5 mmol) in toluene (10 ml) was heated at reflux for 24 hours. The mixture was allowed to cool to 60° C., diluted with isohexane (10 ml) and then cooled to 5° C. The resulting precipitate was collected by filtration, washed with toluene/isohexane (1:1) and dried at 50° C. under vacuum to give the title compound (1.3 g, 70%). NMR: 1.51 (d, 6H), 2.45 (s, 3H), 2.73 (s, 3H), 5.53-5.66 (m, 1H), 7.12 (d, 1H), 7.26 (d, 2H), 7.64 (d, 2H) 8.00 (s, 1H), 8.58 (d, 1H), 9.70 (s, 1H); m/z 340.

[1] See for example Alexandria Journal of Pharmaceutical Sciences (1988), 2(2) 130-2; Archive der Pharmazie (Weinheim, Germany) (1985), 318 (11), 1043-5; and Archive der Pharmazie (Weinheim, Germany) (1979), 312 (5), 426-31

Example 89

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
| --- | --- |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
| --- | --- |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
| --- | --- |
| Compound X | 10 |
| Lactose Ph. Eur | 488.5 |
| Magnesium stearate | 1.5 |

| (e): Injection I | (50 | mg/ml) | |
| --- | --- | --- | --- |
| Compound X | 5.0% | w/v | |
| 1 M Sodium hydroxide solution | 15.0% | v/v | |
| 0.1 M Hydrochloric acid | (to | adjust | pHto7.6) |
| Polyethylene glycol 400 | 4.5% | w/v | |
| Water for injection | to | 100% | |

| (f): Injection II | 10 | mg/ml |
| --- | --- | --- |
| Compound X | 1.0% | w/v |
| Sodium phosphate BP | 3.6% | w/v |
| 0.1 M Sodium hydroxide solution | 15.0% | v/v |
| Water for injection | to | 100% |

| (g): Injection III | (1 | mg/ml,bufferedtopH6) |
| --- | --- | --- |
| Compound X | 0.1% | w/v |
| Sodium phosphate BP | 2.26% | w/v |
| Citric acid | 0.38% | w/v |
| Polyethylene glycol 400 | 3.5% | w/v |
| Water for injection | to | 100% |

Note

The above formulations may be obtained by conventional procedures well known in the pharmaceutical art. The tablets (a)-(c) may be enteric coated by conventional means, for example to provide a coating of cellulose acetate phthalate.

The invention claimed is:

1. A compound of the formula (IA), (IB), (IC), (ID), (IE) and (IF) of the generic structure of formula (I):

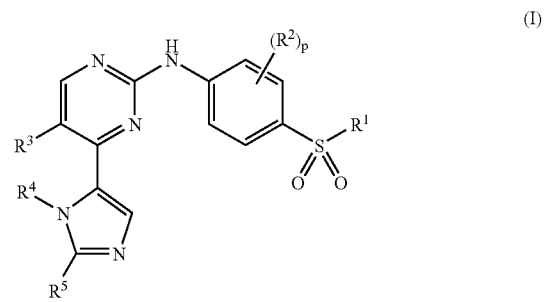

(I)

wherein:
i) a compound of formula (IA) is selected from:

(IA)

wherein:
R¹ is 2-(pyrazolyl-1-yl)ethyl, 3-(isoxazol-3-yloxy)propyl, 2-(thiazol-3-yloxy)ethyl, 2-(thiadiazol-3-yloxy)ethyl, 1,3-dihydroxyprop-2-yl, 1-methyl-1-hydroxymethylethyl, 1,2-dimethylpropyl, 1-methylcyclopropyl, 2,2-dimethylaziridin-1-yl, t-butyl, 2-morpholino-1,1-dimethylethyl, 2-pyrrolidin-1-yl-1,1-dimethylethyl, 2-methylthio-1,1-dimethylethyl, 1,3-dimethoxyprop-2-yl, 1-methoxyprop-2-yl, 1-hydroxyprop-2-yl, 1-ethoxyprop-2-yl, 1-propoxyprop-2-yl, ethoxyethyl or 2-methoxy-1,1-dimethylethyl; and
R² is hydrogen;
or a pharmaceutically acceptable salt or an in vivo hydrolysable ester thereof;

ii) a compound of formula (IB) is selected from:

(IB)

wherein:
R¹ is pyrid-2-ylmethyl, 2-(2-methyl-1,2,4-triazol-5-yl)ethyl, 2-pyrid-2-ylethyl, 2-pyridazin-3-ylethyl, 2-(3,5-dimethyltriazol-4-yl)ethyl, 2-pyrid-3-ylethyl, 2-methoxyethyl, 3-(5-methylpyrazol4-yl)propyl, 2-trifluoromethylpyrid-5-ylmethyl, 2-pyridazin-4-ylethyl, 1,1-dimethylpropyn-2-yl or 2-ethoxyethyl; and
R² is hydrogen or cyano;
or a pharmaceutically acceptable salt thereof;
provided that when R¹ is 2-methoxyethyl, R² is cyano;

iii) a compound of formula (IC) is selected from:

(IC)

wherein:
R¹ is hydrogen, $C_{1-6}$alkyl or $C_{1-6}$alkoxy$C_{1-6}$alkyl;
R² is hydrogen, halo or cyano;
or a pharmaceutically acceptable salt thereof;
provided that when R¹ is 2-methoxyethyl, R² is not hydrogen;

iv) a compound of formula (ID) is selected from:

(ID)

wherein:
R¹ is hydrogen, $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein R¹ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;
R² is hydrogen, halo or cyano;
R³ is $C_{2-6}$alkyl;
or a pharmaceutically acceptable salt thereof;

v) a compound of formula (IE) is selected from:

(IE)

wherein:
R¹ is hydrogen, $C_{1-4}$alkyl, $C_{2-4}$alkenyl, $C_{2-4}$alkynyl, $C_{3-6}$cycloalkyl, $C_{3-6}$cycloalkyl$C_{1-3}$alkyl, a heterocyclyl or heterocyclyl$C_{1-3}$alkyl; wherein R¹ may be optionally substituted on carbon by one or more methyl, ethyl, methoxy, ethoxy, propoxy, trifluoromethyl, trifluoromethoxy, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;
R² is halo, cyano, $C_{1-3}$alkyl or $C_{1-3}$alkoxy;
p is 1-2; wherein the values of R² may be the same or different;
R³ is hydrogen, halo or cyano;
R⁴ is $C_{1-4}$alkyl;
or a pharmaceutically acceptable salt thereof;

provided that said compound is not 4-(1,2-dimethylimidazol-5-yl)-2-[2-methoxy-4-(N-methylsulphamoyl)-5-methylanilino]pyrimidine;

vi) a compound of formula (IF) is selected from:

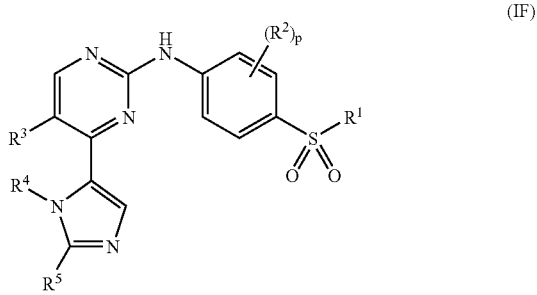

wherein:
R¹ is C$_{1-4}$alkyl, C$_{2-4}$alkenyl, C$_{2-4}$alkynyl, C$_{3-6}$cycloalkyl, C$_{3-6}$cycloalkylC$_{1-3}$alkyl, a heterocyclyl or heterocyclylC$_{1-3}$alkyl; wherein R¹ may be optionally substituted on carbon by one or more methyl, ethyl, methoxy, ethoxy, propoxy, trifluoromethyl, trifluoromethoxy, dimethylamino, 2,2,2-trifluoroethoxy or cyclopropylmethoxy; and wherein if said heterocyclyl contains an —NH— moiety that nitrogen may be optionally substituted by one or more methyl, ethyl, acetyl, 2,2,2-trifluoroethyl or methoxyethyl;

R² is halo, cyano, C$_{1-3}$alkyl or C$_{1-3}$alkoxy;

p is 0-2; wherein the values of R² may be the same or different;

R³ is hydrogen, halo or cyano;

R⁴ is C$_{2-6}$alkyl;

R⁵ is C$_{1-6}$alkyl or C$_{2-6}$alkenyl; wherein R⁵ may be optionally substituted on carbon by one or more methoxy, ethoxy, propoxy, trifluoromethyl, trifluoromethoxy, 2,2,2-trifluoroethoxy or cyclopropylmethoxy;

or a pharmaceutically acceptable salt thereof.

2. The compound of formula (I) according to claim 1 which is a compound of formula (IA), or a pharmaceutically acceptable salt or an in vivo hydrolysable ester thereof.

3. The compound of formula (IA) according to claim 2 selected from:
2-{4-[N-(2-ethoxyethyl)sulphamoyl]anilino}-4-(1,2-dimethylimidazol-5-yl)pyrimidine;
2-{4-[N-(t-butyl)sulphamoyl]anilino}-4-(1,2-dimethylimidazol-5-yl)pyrimidine;
2-{4-[N-(1-ethoxyprop-2-yl)sulphamoyl]anilino}-4-(1,2-dimethylimidazol-5-yl)pyrimidine;
2-{4-[N-(1-propoxyprop-2-yl)sulphamoyl]anilino}-4-(1,2-dimethylimidazol-5-yl)pyrimidine; and
2-{4-[N-(1-methylcyclopropyl)sulphamoyl]anilino}-4-(1,2-dimethylimidazol-5-yl)pyrimidine;
or a pharmaceutically acceptable salt thereof.

4. The compound of formula (I) according to claim 1 which is a compound of formula (IB), or a pharmaceutically acceptable salt thereof.

5. The compound of formula (IB) according to claim 4 selected from:
4-(1-ethyl-2-methylimidazol-5-yl)-2-{4-[N-(2-ethoxyethyl)sulphamoyl]anilino}pyrimidine; and
2-{4-[N-(1,1-dimethylprop-2-ynyl)sulphamoyl]anilino}-4-(1-ethyl-2-methylimidazol-5-yl)pyrimidine;
or a pharmaceutically acceptable salt thereof.

6. The compound of formula (I) according to claim 1 which is a compound of formula (IC), or a pharmaceutically acceptable salt thereof.

7. The compound of formula (IC) according to claim 6, or a pharmaceutically acceptable salt thereof; wherein
R¹ is hydrogen, 2-methoxyethyl, methyl or 2-ethoxyethyl; and
R² is hydrogen or bromo;
provided that when R¹ is 2-methoxyethyl R² is not hydrogen.

8. The compound of formula (IC) according to claim 6 selected from:
4-(1-isopropyl-2-methylimidazol-5-yl)-2-{4-[N-(2-ethoxyethyl)sulphamoyl]anilino}pyrimidine; and
4-(1-isopropyl-2-methylimidazol-5-yl)-2-{4-[N-(methyl)sulphamoyl]anilino}pyrimidine;
or a pharmaceutically acceptable salt thereof.

9. The compound of formula (I) according to claim 1 which is a compound of formula (ID), or a pharmaceutically acceptable salt thereof.

10. The compound of formula (ID) according to claim 9, or a pharmaceutically acceptable salt thereof; wherein
R¹ is cyclopropyl, 2-methoxyethyl or tetrahydrofur-2-ylmethyl;
R² is hydrogen; and
R³ is ethyl or isopropyl.

11. The compound of formula (ID) according to claim 9 selected from:
4-(1-isopropylimidazol-5-yl)-2-{4-[N-(cyclopropyl)sulphamoyl]anilino}pyrimidine;
4-(1-isopropylimidazol-5-yl)-2-{4-[N-(tetrahydrofur-2-ylmethyl)sulphamoyl]anilino}pyrimidine;
4-(1-ethylimidazol-5-yl)-2-{4-[N-(2-methoxyethyl)sulphamoyl]anilino}pyrimidine; and
4-(1-isopropylimidazol-5-yl)-2-{4-[N-(2-methoxyethyl)sulphamoyl]anilino}pyrimidine;
or a pharmaceutically acceptable salt thereof.

12. The compound of formula (I) according to claim 1 which is a compound of formula (IE), or a pharmaceutically acceptable salt thereof.

13. The compound of formula (IE) according to claim 12, or a pharmaceutically acceptable salt thereof; wherein
R¹ is hydrogen or 2-methoxyethyl;
R² is fluoro;
p is 1;
R³ is hydrogen; and
R⁴ is methyl.

14. The compound of formula (IE) according to claim 12 selected from:
2-{4-[N-(2-methoxyethyl)sulphamoyl]-2-fluoroanilino}-4-(1,2-dimethylimidazol-5-yl)pyrimidine; and
2-(4-sulphamoyl-2-fluoroanilino)-4-(1,2-dimethylimidazol-5-yl)pyrimidine;
or a pharmaceutically acceptable salt thereof.

15. The compound of formula (I) according to claim 1 which is a compound of formula (IF), or a pharmaceutically acceptable salt thereof.

16. The compound of formula (IF) according to claim 15, or a pharmaceutically acceptable salt thereof; wherein
R¹ is methyl, 3-dimethylaminopropyl, 3-methoxypropyl, 3,3,3-trifluoropropyl or butyl;
p is 0;
R³ is hydrogen;
R⁴ is isopropyl; and
R⁵ is methyl.

17. The compound of formula (IF) according to claim 15 selected from:

4-(1-isopropyl-2-methylimidazol-5-yl)-2-(4-mesylanilino)pyrimidine;

4-(1-isopropyl-2-methylimidazol-5-yl)-2-[4-(3-methoxypropylsulphonyl)anilino]pyrimidine; and 4-(1-isopropyl-2-methylimidazol-5-yl)-2-[4-(3-N,N-dimethylaminopropylsulphonyl)anilino]pyrimidine;

or a pharmaceutically acceptable salt thereof.

18. A pharmaceutical composition which comprises a compound of formula (I), or a pharmaceutically acceptable salt or in vivo hydrolysable ester thereof, according to claim 1, in association with a pharmaceutically-acceptable diluent or earner.

19. A method for treating rheumatoid arthritis in a warm-blooded animal in need thereof, which comprises administering to said animal an effective amount of a compound of formula (I) or a pharmaceutically acceptable salt or in vivo hydrolysable ester thereof as claimed in claim 1.

* * * * *